(12) United States Patent
Katzenmaier et al.

(10) Patent No.: US 7,899,681 B2
(45) Date of Patent: Mar. 1, 2011

(54) ELECTRONIC MANAGEMENT OF STERILIZATION PROCESS INFORMATION

(75) Inventors: Kevin R. Katzenmaier, Woodbury, MN (US); Janet M. Prust, Stillwater, MN (US); Andrew C. Daus, St. Louis, MO (US)

(73) Assignee: 3M Innovative Properties Company, St. Paul, MN (US)

( * ) Notice: Subject to any disclaimer, the term of this patent is extended or adjusted under 35 U.S.C. 154(b) by 3509 days.

(21) Appl. No.: 10/113,923

(22) Filed: Mar. 29, 2002

(65) Prior Publication Data

US 2003/0187586 A1    Oct. 2, 2003

(51) Int. Cl.
*G06Q 10/00*    (2006.01)
(52) U.S. Cl. ............... 705/2; 702/19; 422/22; 424/449; 436/1
(58) Field of Classification Search ............. 705/2–3; 422/55, 22; 702/19; 424/449; 436/1
See application file for complete search history.

(56) References Cited

U.S. PATENT DOCUMENTS

| | | | | |
|---|---|---|---|---|
| 4,255,750 | A * | 3/1981 | Riley | 343/703 |
| 5,565,634 | A * | 10/1996 | Graessle et al. | 73/865.9 |
| 6,063,591 | A | 5/2000 | Bolea | |
| 2002/0087101 | A1* | 7/2002 | Barrick et al. | 600/587 |
| 2003/0039579 | A1* | 2/2003 | Lambert et al. | 422/22 |
| 2004/0142022 | A1* | 7/2004 | Shudo et al. | 424/449 |

FOREIGN PATENT DOCUMENTS

WO    WO 01/10476    2/2001

OTHER PUBLICATIONS

"Controlling and Improving the Sterilization Process Using Biological and Chemical Indicators," http://www.iceinstitute.com, 2001.
"IMPRESS™ Instrument Management Software System," http://www.allegiance.net/literate/impress/cover.htm.
"Sterile Processing Microsystem," http://www.mmmicrosystems.com/spm.html.
"The T-DOC™ 1000 Guide," Getinge Castle, Inc.
"ALISA Sterilisation Tracking System," http://www.sharknet.hl.com.au/alisasys.htm.
"JARIT Instruments," http://www.jarit.com/.
"Instrument Control System," http://www.ipathsoftware.com/software/ics.htm.
"ABGI Product 3," http://www.abgi.net/prod03.htm.
"Rosebud Products & Services," http://www.rosebudsolutions.com/products/1product.htm.
"Accutrac," http://www.censis.net/accutrac.asp.

* cited by examiner

*Primary Examiner* — Vanel Frenel
(74) *Attorney, Agent, or Firm* — X. Christina Huang

(57) ABSTRACT

A system for electronic management of information relating to sterilization and high level disinfection process monitoring generates electronic sterilization record for sterilized and high level disinfected loads, and optically scans sterilization monitors associated with the sterilized loads. The system stores a digital representation of each scanned sterilization monitor, and associates the digital representation with the electronic sterilization record. The electronic sterilization record also may contain a variety of information including a sterilization status data entered by a user. The system permits a user to review both the sterilization status information and the digitized representation of the sterilization monitor online to verify accuracy. In this manner, a representation of the actual sterilization monitor can be stored and retrieved when desired for verification of result, audits and other quality review activity.

39 Claims, 30 Drawing Sheets

Customize: 01

Process Type: Steam - Vacuum Assist

Process Parameters

| Parameter | Units | Minimum | Default | Maximum |
|---|---|---|---|---|
| Cycle Time | mm:ss | 10:00 | 12:00 | 14:00 |
| Sterilization Time | mm:ss | 03:00 | 04:00 | 05:00 |
| Temperature | °C | 132 | 132 | 135 |
| Pressure | psi | 41.8 | 41.8 | 42.8 |
| | (None) | | | |
| | (None) | | | |
| | (None) | | | |
| | (None) | | | |
| | (None) | | | |
| | (None) | | | |
| | (None) | | | |
| | (None) | | | |

Make:

Model:

Serial Number:

FIG. 7

| Customize: 01 | | | | |
|---|---|---|---|---|
| Process Type: | Steam - Vacuum Assist | | | |

| Process Parameters | | | | |
|---|---|---|---|---|
| Parameter | Units | Minimum | Default | Maximum |
| Cycle Time | mm:ss | 10:00 | 12:00 | 14:00 |
| Sterilization Time | mm:ss | 03:00 | 04:00 | 05:00 |
| Temperature | mm:ss | 132 | 132 | 135 |
| Pressure | hh:mm | 41.8 | 41.8 | 42.8 |
| | minutes | | | |
| | hours | | | |
| | ... | | | |
| | % | | | |
| | Date | | | |

FIG. 8

Final Load Status Designations by Operator

| Operator | Released | B-D Passed | Sterilizer Passed | Quarantine | Aborted | Failed | In Recall / Recalled |
|---|---|---|---|---|---|---|---|
| Anne | 0 | 0 | 0 | 0 | 0 | 0 | 0 |
| Elsa | 2 | 0 | 0 | 0 | 0 | 0 | 0 |
| Kevn | 3 | 3 | 0 | 0 | 0 | 0 | 0 |

Report from 3/14/01 through 3/14/01

FIG. 29

Processing History by BI Test and Control Results

| Sterilizer | Process | Total BI Loads | Rapid Result Positive Test | Rapid Result Negative Control | Growth Results Positive Test | Growth Results Negative Control |
|---|---|---|---|---|---|---|
| 01 | Steam - Vacuum Assist | 3 | 0 | 0 | 0 | 0 |
| 02 | Steam - Vacuum Assist | 2 | 0 | 0 | 0 | 0 |
| 04 | Ethylene Oxide | 1 | 0 | 0 | 0 | 0 |

Report from 3/14/01 through 3/14/01

FIG. 30

Processing History by Bowie-Dick Type Test Results

| Sterilizer | Total Bowie-Dick Type Loads | Pass Results | Failed Results |
|---|---|---|---|
| 01 | 1 | 1 | 0 |
| 02 | 1 | 1 | 0 |
| 03 | 1 | 1 | 0 |

Report from 3/14/01 through 3/14/01

FIG. 31

Processing History by Destination

Processing History by Destination
Report from 3/14/01 through 3/14/01

| Destination | Total Load Items | Steam | EO | Liquid Peracetic Acid | H2O2/ Gas Plasma | High Level Disinfect | Other |
|---|---|---|---|---|---|---|---|
| Cath Lab | 10 | 10 | 0 | 0 | 0 | 0 | 0 |
| Clinic 1 | 2 | 2 | 0 | 0 | 0 | 0 | 0 |
| ER | 15 | 15 | 0 | 0 | 0 | 0 | 0 |
| ICU 1 | 5 | 5 | 0 | 0 | 0 | 0 | 0 |
| ICU 2 | 4 | 4 | 0 | 0 | 0 | 0 | 0 |
| Labor & Delivery 1 | 4 | 4 | 0 | 0 | 0 | 0 | 0 |
| Labor & Delivery 2 | 4 | 4 | 0 | 0 | 0 | 0 | 0 |
| OR 1 | 12 | 12 | 0 | 0 | 0 | 0 | 0 |
| OR 2 | 10 | 10 | 0 | 0 | 0 | 0 | 0 |
| OR 3 | 19 | 13 | 6 | 0 | 0 | 0 | 0 |
| Out Pt Surg | 8 | 8 | 0 | 0 | 0 | 0 | 0 |

FIG. 32

Processing History by Load Item

Processing History by Load Item
Report from 3/14/01 through 3/14/01

| Load Item | Number of Times Processed |
|---|---|
| Angio Tray | 6 |
| Arterial Cannula Tray | 4 |
| Bone Graft Inst. | 1 |
| Cardiac Cath Vascular Set | 3 |
| Cardiology Pac | 1 |
| Compression Hip Inst | 2 |
| Craniotomy Set | 1 |
| C-Section | 6 |
| D&C Set | 2 |
| G I Set | 3 |
| Gallbladder Set | 4 |
| General Set | 13 |

FIG. 33

Processing History by Sterilizer

Processing History by Sterilizer
Report from 3/14/01 through 3/14/01

| Sterilizer | Process | Total Loads | Release | B-D Passed | Sterilizer Passed | Aborted | Quar | Failed | Recall | Waiting for Final Status |
|---|---|---|---|---|---|---|---|---|---|---|
| 01 | Steam - Vacuum Assist | 5 | 4 | 1 | 0 | 0 | 0 | 0 | 0 | 0 |
| 02 | Steam - Vacuum Assist | 3 | 2 | 1 | 0 | 0 | 0 | 0 | 0 | 0 |
| 03 | Steam - Vacuum Assist | 1 | 0 | 1 | 0 | 0 | 0 | 0 | 0 | 0 |
| 04 | Ethylene Oxide | 1 | 0 | 0 | 0 | 0 | 0 | 0 | 0 | 1 |

FIG. 34

Processing History by Process Parameters

Processing History by Process Parameters
Report from 3/14/01 through 3/14/01

| Sterilizer | Process | Total Loads | Pass Results | Fail Results |
|---|---|---|---|---|
| 01 | Steam - Vacuum Assist | 4 | 4 | 0 |
| 02 | Steam - Vacuum Assist | 3 | 3 | 0 |
| 03 | Steam - Vacuum Assist | 1 | 1 | 0 |
| 04 | Ethylene Oxide | 1 | 1 | 0 |

FIG. 35

ELECTRONIC MANAGEMENT OF STERILIZATION PROCESS INFORMATION

TECHNICAL FIELD

The invention relates to the sterilization processing and, more particularly, to maintenance of information relating to sterilization processing and monitoring within a sterilization facility.

BACKGROUND

In a health care facility, sterilization generally refers to the process of eliminating all bacteria and other living organisms from the surfaces of instruments, medical devices, implants and other articles used in sterile surgical procedures. High level disinfection generally refers to a process of eliminating most bacteria and other microorganisms, except spores, on instruments and other articles used in certain surgical procedures. A traditional thermal sterilization process uses steam under pressure. Low-temperature chemical sterilization processes use ethylene oxide, hydrogen peroxide, hydrogen peroxide/plasma, or peracetic acid in vapor form as the sterilant, as well as gamma irradiation and electron beam sterilization. In each process, the sterilizer is designed to kill all viable living organisms within a sterilization chamber. To achieve this objective, health care personnel must select the appropriate sterilization process and carefully monitor its parameters and employ adequate preparation, packaging and sterilizer loading techniques.

To verify successful sterilization, health care facilities typically use sterilization process monitors. A sterilization process monitor is a device that measures and displays information to indicate whether a sterilization cycle met the required conditions necessary to achieve sterilization. Examples of sterilization monitors include: biological indicators, chemical indicators, chemical integrators, Bowie-Dick test packs, and challenge packs. A chemical sterilization monitor, for example, responds to one or more conditions necessary for proper sterilization, such as temperature, time, and sterilant concentration or exposure. A biological monitor carries a biological agent, and indicates successful sterilization when the biological agent has been killed. The chemical monitor is typically placed within a specific device pack or within a load containing articles to be sterilized. The biological monitor is typically placed in a test package within a load containing articles to be sterilized.

Another form of monitor is a sterilizer strip, sometimes referred to as a mechanical monitor. A sterilizer strip may take the form of a graph or printout from a sterilizer that records cycle parameters like time, temperature and pressure during a sterilization cycle. Thus, the sterilization strip serves as a record of the measured conditions.

Following the sterilization process, the chemical sterilization monitor aids sterilization personnel, e.g., in a health care facility, in identifying loads that have been exposed to the conditions necessary for sterilization. The load may carry other information, often incorporated within the monitor, that identifies the load for record-keeping purposes. For example, a monitor, such as a chemical monitor or a sterilization strip, may carry text or bar code information that uniquely identifies the load.

To achieve effective sterilization workflow, record-keeping, and safety, a health care facility must devote substantial resources, personnel, training and administrative resources to the sterilization process. In particular, it is necessary to maintain accurate records of sterilization processes to enable better quality control and verify compliance with applicable standards. Regulatory agencies and independent audit organizations may require access to sterilization records for verification of regulatory compliance or accreditation. Accordingly, orderly and comprehensive record-keeping is important to a sterilization facility.

SUMMARY

In general, the invention is directed to electronic management of sterilization process information and high level disinfection process information. The invention may involve generation of electronic sterilization records for individual or multiple sterilized loads. A sterilization record may contain a variety of information entered by a user concerning the sterilization process monitoring status of a particular load. According to one aspect of the invention, the sterilization record may include a digital image of a sterilization monitor or monitors associated with the sterilized load.

The sterilization monitor can be optically scanned to form the digital image. The scanning operation may form an integral part of the process of generating the sterilization record. In this manner, the sterilization record may include not only sterilization data entered by a user upon visual inspection of the sterilization monitor, but also a digital image of the sterilization monitor itself for online review. For example, the sterilization record may include a digital image of a sterilization monitor such as a chemical indicator or sterilizer strip, if applicable. Sterilization monitors such as chemical indicators, biological indicators, chemical integrators, Bowie-Dick test packs, challenge packs, sterilizer strips and the like may be referred to herein in similar terminology as a sterilization monitor. Online availability of a digital image of a sterilization monitor may be highly advantageous in verifying the accuracy of the sterilization data entered by the user.

A user may compare the indication conveyed by the digital image to the sterilization data, for example, contemporaneously with generation of the sterilization record or during a subsequent quality review inspection or compliance audit. Sterilization monitors, including sterilizer strips, can be susceptible to degradation such as fading, curling, reverse color change, or other damage that can affect the quality and readability of the information carried by the monitor or strip. The digital image provides an accurate and persistent record of the actual condition of the sterilization monitor, e.g., a chemical indicator or sterilizer strip, at the time a sterilization record was generated, as well as the result indicated by the monitor. For convenience, the digital image can be retrieved and displayed with the sterilization process monitor record or, as referred to herein, a sterilization record.

As another aspect of the invention, authorization to create, modify or access the electronic sterilization records may be restricted by selectively granting different levels of permission to particular users. Access to the electronic sterilization records may be made directly via a computer containing an archive of the records or remotely via a network connection to the computer. Upon access, the user may perform a variety of searches of the electronic sterilization records to generate search results or reports containing desired sterilization process monitor information.

In one embodiment, the invention provides a method comprising generating an electronic sterilization record for a sterilized load, and optically scanning a sterilization monitor associated with the sterilized load. The method further involves storing a digital representation of the scanned sterilization monitor, and associating the stored digital representation with the electronic sterilization record.

In another embodiment, the invention provides a system comprising a computer that generates an electronic sterilization record for a sterilized load, and a scanner that optically scans a sterilization monitor associated with the sterilized load. A storage device stores a digital representation of the scanned sterilization monitor, and the computer associates the digital representation with the electronic sterilization record.

In an added embodiment, the invention provides a computer-readable medium carrying instructions to cause a programmable processor to generate an electronic sterilization record for a sterilized load, control a scanner to optically scan a sterilization monitor associated with the sterilized load, store a digital representation of the scanned sterilization monitor, and associate the digital representation with the electronic sterilization record.

In a further embodiment, the invention provides a method comprising generating an electronic sterilization record for a sterilized load, optically scanning a sterilization monitor associated with the sterilized load, storing a digital representation of the scanned sterilization monitor, and associating the stored digital representation with the electronic sterilization record. The method further involves receiving information from a first user indicating a sterilization condition of the sterilized load, associating the received information with the electronic sterilization record, and presenting the electronic sterilization record to a second user for comparison of the information received from the first user to the digital representation of the scanned sterilization monitor. Indication of a sterilization condition, as used herein, may refer to indication of the result of monitoring one or more parameters providing an indication that conditions for successful sterilization were met.

In another embodiment, the invention provides a system comprising a computer that generates an electronic sterilization record for a sterilized load, and an optical scanner that scans a sterilization monitor associated with the sterilized load, wherein the computer stores a digital representation of the scanned sterilization monitor, and associates the digital representation with the electronic sterilization record. A user input device receives information from a first user indicating a sterilization condition of the sterilized load, wherein the computer associates the received information with the electronic sterilization record. A user output device presents the electronic sterilization record to a second user for comparison of the information received from the first user to the stored digital representation of the scanned sterilization monitor.

In an added embodiment, the invention provides a computer-readable medium carrying instructions to cause a programmable processor to generate an electronic sterilization record for a sterilized load, control an optical scanner to scan a sterilization monitor associated with the sterilized load, store a digital representation of the scanned sterilization monitor, and associate the stored digital representation with the electronic sterilization record. In response to the instructions, the computer also may receive information from a first user indicating a sterilization condition of the sterilized load, associate the received information with the electronic sterilization record, and present the electronic sterilization record to a second user for comparison of the information received from the first user to the stored digital representation of the scanned sterilization monitor.

In a further embodiment, the invention provides an electronic sterilization record stored on a computer-readable medium. The electronic sterilization record comprises information entered by a user representing a sterilization condition of a sterilized load, and a digital representation of a scanned sterilization monitor associated with the sterilized load.

The invention may provide one or more advantages. In general, the invention enables automated management of sterilization process information using electronic sterilization records. The electronic sterilization records can be conveniently archived and sorted according to a variety of characteristics such as sterilizer, sterilized load, process type, load item, user identity, destination, pass/fail status, and the like. In addition, the electronic sterilization records may include both information entered by a user representing a condition of a sterilized load, as well as a digital representation of one or more scanned sterilization monitors associated with the sterilized load.

The electronic sterilization record provides a persistent record of the actual sterilization process monitor results that is conveniently accessible by other users. In particular, unlike the original sterilization monitor, the scanned sterilization monitor is not prone to degradation such as fading, curling, reverse color change, or other damage that can affect accuracy, and indicates the actual condition of the sterilization monitor at the time of use. In general, the scanned sterilization monitor also cannot be misplaced, and is less likely to be filed incorrectly.

As an illustration, a user may retrieve a sterilization record from the archive and compare the information entered earlier by a different user to the condition indicated by the scanned sterilization monitor. The comparison may be part of a review or "double-checking" process performed within a sterilization facility to verify accuracy and thereby promote safety. Moreover, management, quality review or compliance audit personnel may retrieve electronic sterilization records at a later time to verify accuracy and compliance with applicable standards.

One or more scanned sterilization monitors may be conveniently presented with the contents of the electronic sterilization record on a display device, e.g., as a thumbnail image with a hyperlink to a larger image. In addition, the sterilization record may be accessed remotely via a computer network. The user may annotate the electronic sterilization record or the scanned monitor itself to document information that may be of interest in a subsequent review of the sterilization facility.

A further advantage, the accuracy of the electronic sterilization records may be protected by a variety of procedural safeguards such as user authorization and permissions. For example, in addition to requiring password access for users to create, modify or access electronic sterilization records, the scope of user access may be restricted by a set of predefined permissions. In particular, users may be given permission for creation, modification and access to electronic sterilization records for selected sterilizers, destinations, process types, and the like.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 7 illustrates an example user interface screen presenting customization of process type parameters for a sterilizer.

FIG. 8 illustrates another example user interface screen presenting customization of process type parameters for a sterilizer.

FIGS. 29-35 illustrate portions of user interface screens presenting reports generated for a variety of search criteria.

DETAILED DESCRIPTION

Figure 1:
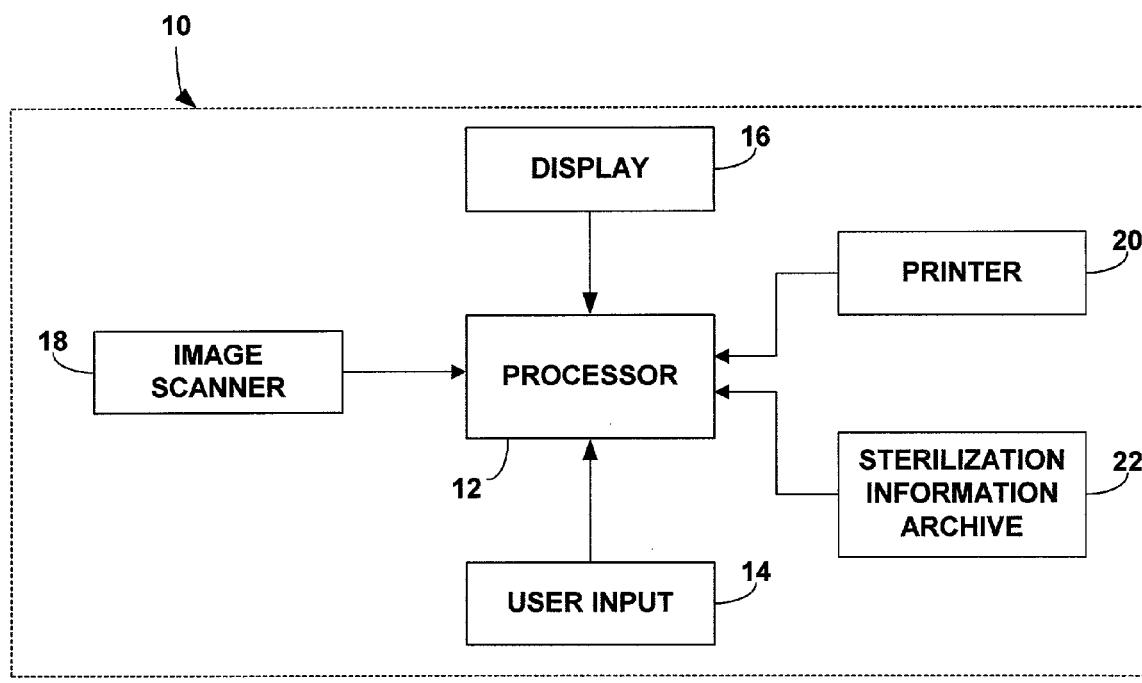
FIG. 1 is a block diagram illustrating an example system for electronic management of sterilization and high level disinfection process monitoring information.

FIG. 1 is a block diagram illustrating an example system 10 for electronic management of sterilization information and high level disinfection information. As shown in FIG. 1, system 10 may include a processor 12, user input device 14, display device 16, an image scanner 18, printer 20 and a sterilization information archive 22. Processor 12 executes instructions embodied in application program code to receive, process and manage sterilization information obtained from user input device 14 and image scanner 18. Archive 22 receives information from processor 12, e.g., in the form of electronic sterilization records, and stores the information for access and retrieval by users of system 10. For example, a user may enter search queries via user input device 14 to access selected sterilization records. Processor 12 may present the sterilization information, in various forms, to users via display device 16 or printer 20.

Processor 12 may take the form of a CPU within a computing device such as a personal computer, workstation, personal digital assistant (PDA), or the like. Archive 22 may take the form of a fixed or removable magnetic or optical media drive that stores sterilization information provided by processor 12. A user may interact with processor 12 via user input device 14 to access and retrieve information from archive 22. Alternatively, a user may interact with processor 12 via a network connection, e.g., via a local area network, wide area network, or the Internet. User input device 14 may take the form of keyboard, a pointing device, or a combination of both. Display device 16 may take the form of a cathode ray tube (CRT) monitor or flat panel display.

System 10 generates electronic sterilization records for individual or multiple sterilized loads, and can be used for automated recordkeeping within a sterilization facility or department. A sterilization record may contain a variety of information entered by a user concerning the sterilization status of a particular load. In addition, a sterilization record may include a digital image of a sterilization monitor associated with the sterilized load. In particular, image scanner 18 scans a sterilization monitor carried by a processed load. The sterilization monitor visibly indicates a result representing a sterilization condition of the sterilized load. For example, the result may take the form of a color change or other visible indication or, in the case of a sterilizer strip, graphic or textual information. In each case, the result is responsive to a monitored parameter associated with the sterilization process.

The sterilization monitor may be a sterilization monitor that measures and displays information to indicate whether a sterilization cycle met the required conditions necessary to achieve sterilization. Examples of sterilization monitors include: biological indicators, chemical indicators, chemical integrators, Bowie-Dick test packs, and challenge packs. Alternatively, the sterilization monitor may be a sterilizer strip. A sterilization strip ordinarily is a graph or printout from a printer or graphing unit associated with a sterilizer. The sterilizer strip printout or graph records cycle parameters like time, temperature and pressure during a sterilization cycle.

Existing biological indicators typically do not convey visually perceptible information that would be useful if scanned. In the event a biological indicator emerges that provides visually perceptible information, however, system 10 may be readily applied to record scanned images of biological indicators, in addition to chemical indicators, chemical integrators, Bowie-Dick type chemical indicators, test packs, sterilizer printout strips or other mechanical monitors, and the like. Also, for biological indicator readers that generate graphic, textual or coded output in response to a reading operation, the output may be scanned. Accordingly, scanning of biological indicators is contemplated in accordance with certain embodiments of the invention.

When a user retrieves a sterilization record in archive 22, display device 16 may display both text information entered by a user and the digital image scanned by scanner 18. Sterilization monitors, such as chemical indicators, sterilizer strips, and the like, can be susceptible to degradation such as fading, curling, reverse color change, or other damage that can affect the quality and readability of the information carried by the monitor or strip. The digital image provides an accurate and persistent record of the actual condition of the sterilization monitor at the time of sterilization.

Figure 2:
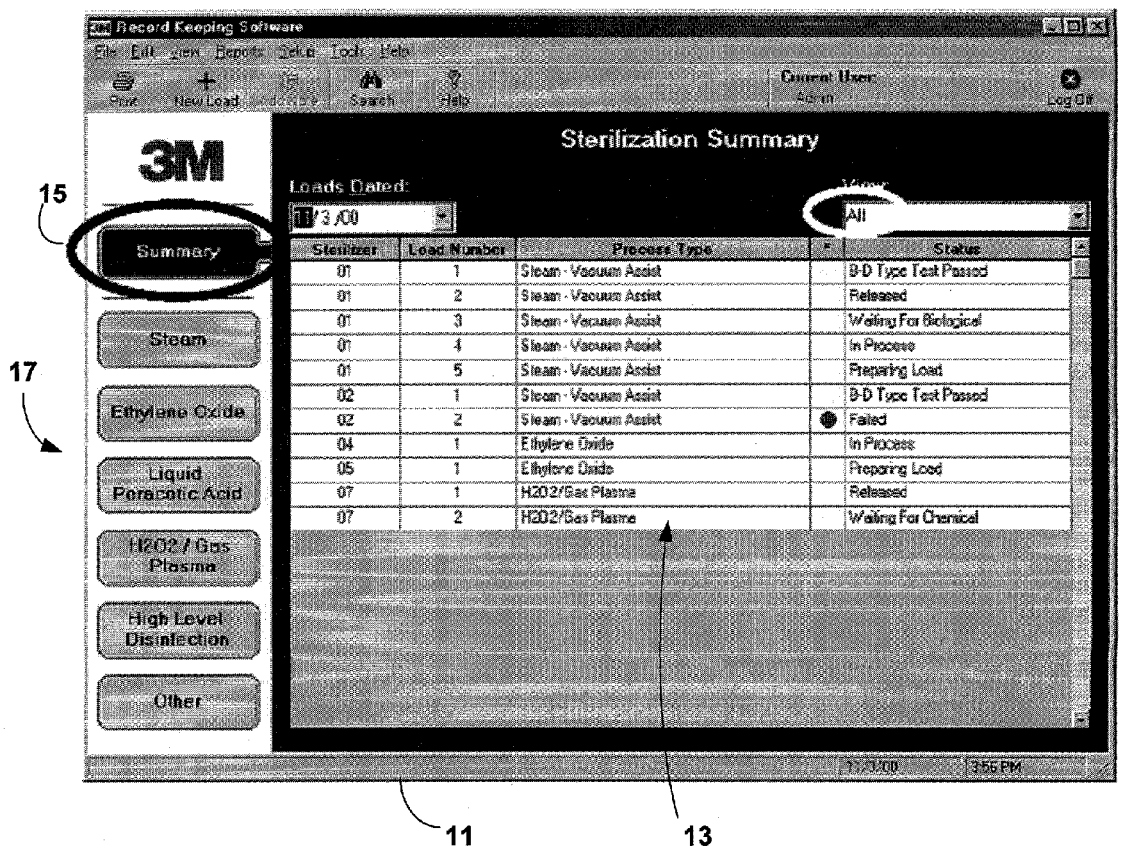
FIG. 2 illustrates an example user interface screen presenting a sterilization process activity summary in the system of FIG. 1.

FIG. 2 illustrates an example user interface screen 11 presenting a sterilization activity summary in the system of FIG. 1. In response to selections made via user input device 14, processor 12 accesses sterilization information archive 22 to retrieve pertinent information, and drives display device 16 to present the information for viewing by a user. As shown in FIG. 2, display device 16 may present a user interface screen 11 with a view of sterilized loads created for a given date, i.e., the sterilized loads entered into system 10 by a user for recordkeeping purposes on that date. The sterilized loads may be recurring in the sense that they are processed on a daily or weekly basis. Alternatively, the sterilized loads may be customized and entered on a one-time basis for recording in system 10.

For each sterilized load, the user interface screen may present a load identifier for unique identification purposes, and a sterilizer identifier indicating the particular sterilizer used to process the load. The load and sterilizer identifiers may be numeric. Reference numeral 13 generally indicates the load information presented to the user. As further shown in FIG. 2, a load number may be reused for loads processed by different sterilizers. For example, sterilizer 01 may process a set of loads 1-5, whereas sterilizer 02 may process a different set of loads 1-2. With the sterilizer identifier and load identifier, the user interface screen also may present the process type, e.g., Steam—Vacuum Assist, Ethylene Oxide, H2O2/Gas Plasma, or the like.

In addition, the user interface screen may present the status of the load, e.g., whether the load is still in process or was successfully processed by the sterilizer. The load status may indicate that a load passed or failed, as verified, for example, by a chemical or biological monitor. Indeed, as shown in FIG. 2, the load status may identify the type of monitor used to verify the status of the load. For example, the user interface screen FIG. 2 indicates that load 1 of sterilizer 01 was successfully processed, as verified by a Bowie-Dick type monitor ("B-D Type Test Passed").

The load status presented by the user interface screen of FIG. 2 also may identify a number of different stages in the sterilization process. For example, some loads may be listed as being in preparation for sterilization ("Preparing Load"), in the course of sterilization ("In Process"), waiting for verification from a chemical or biological monitor ("Waiting for Chemical," "Waiting for Biological"), or released for use ("Released").

Processor 12 may receive input from a user in the form of mouse clicks, drop-down menu selections, text input, and the like, entered with a keyboard, pointing device, or both. In the example of FIG. 2, the user has selected the "Summary" button, which is circled for purposes of illustration and generally identified by reference numeral 15. In response, processor 12 drives display device 16 to present information concerning loads processed by a set of sterilizers, including sterilizers that operate according to different process types.

As an alternative, a user may select a category of process types, e.g., by clicking a particular button ("Steam," "Ethylene Oxide," "Liquid Peracetic Acid," "H2O2/Gas Plasma," "High Level Disinfection," or "Other") with a pointing device such as a mouse. The process type section buttons are identified generally by reference numeral 17. Upon selection of one of buttons 17, processor 12 accesses sterilization information archive 22 to retrieve pertinent information relating to the selected process type. Using the retrieved information, processor 12 drives display device 16 to present only those load items processed by sterilizers of the selected process type.

Figure 3:
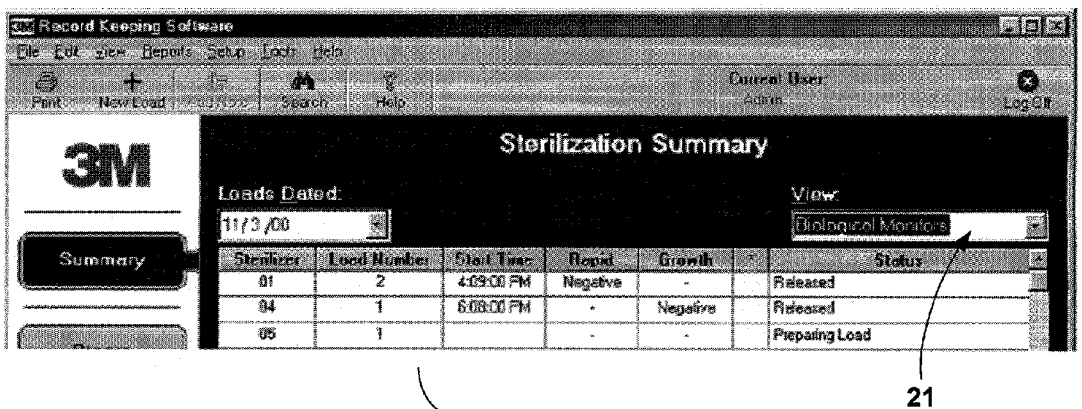
FIG. 3 illustrates an example user interface screen presenting a summary for a subset of device processing activities.

FIG. 3 illustrates a portion of an example user interface screen 19 presenting a summary for a subset of sterilization activities. In addition to selecting a process type or date range, the user may limit the displayed contents of user interface screen 19 by selecting different categories in the "View" drop-down menu 21. In the example of FIG. 1, user interface screen 19 shows information for "All" sterilized loads. In the example of FIG. 3, however, the contents of user interface screen 19 is limited to loads processed using biological monitors. Other categories listed in drop-down menu 21 may be biological monitors, chemical monitors, or Bowie-Dick type tests.

Figure 4:
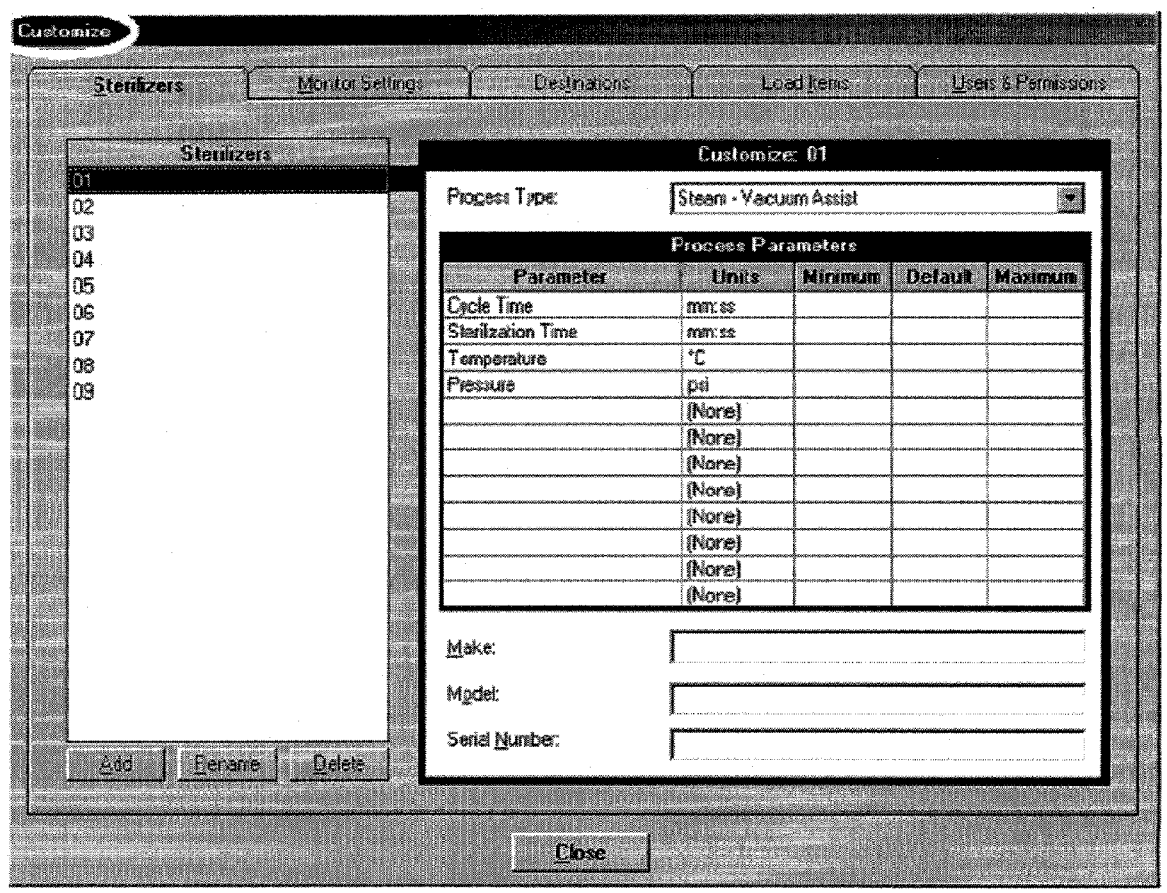
FIG. 4 illustrates an example user interface screen presenting a customization window.

FIG. 4 illustrates an example user interface screen presenting customization options for a sterilizer. In the example of FIG. 4, a process type and parameter range customization window is displayed for a sterilizer assigned ID code "01." Customization may involve identification of a sterilization process type and ID code for each sterilizer used at a facility. In addition, a user may customize other information categories such as monitor settings for each process, load destinations, load label format, names of load items, contents of load items, names of users, and authorization levels for individual users, i.e., user permissions. Much of the customization process may be completed during an initial setup of system 10. Following initial setup, system 10 may be further customized from time-to-time, e.g., as equipment or personnel change for the particular sterilization facility. The person responsible for customization may be a sterile processing supervisor or an information technology (IT) system administrator for the sterilization facility.

Figure 5:
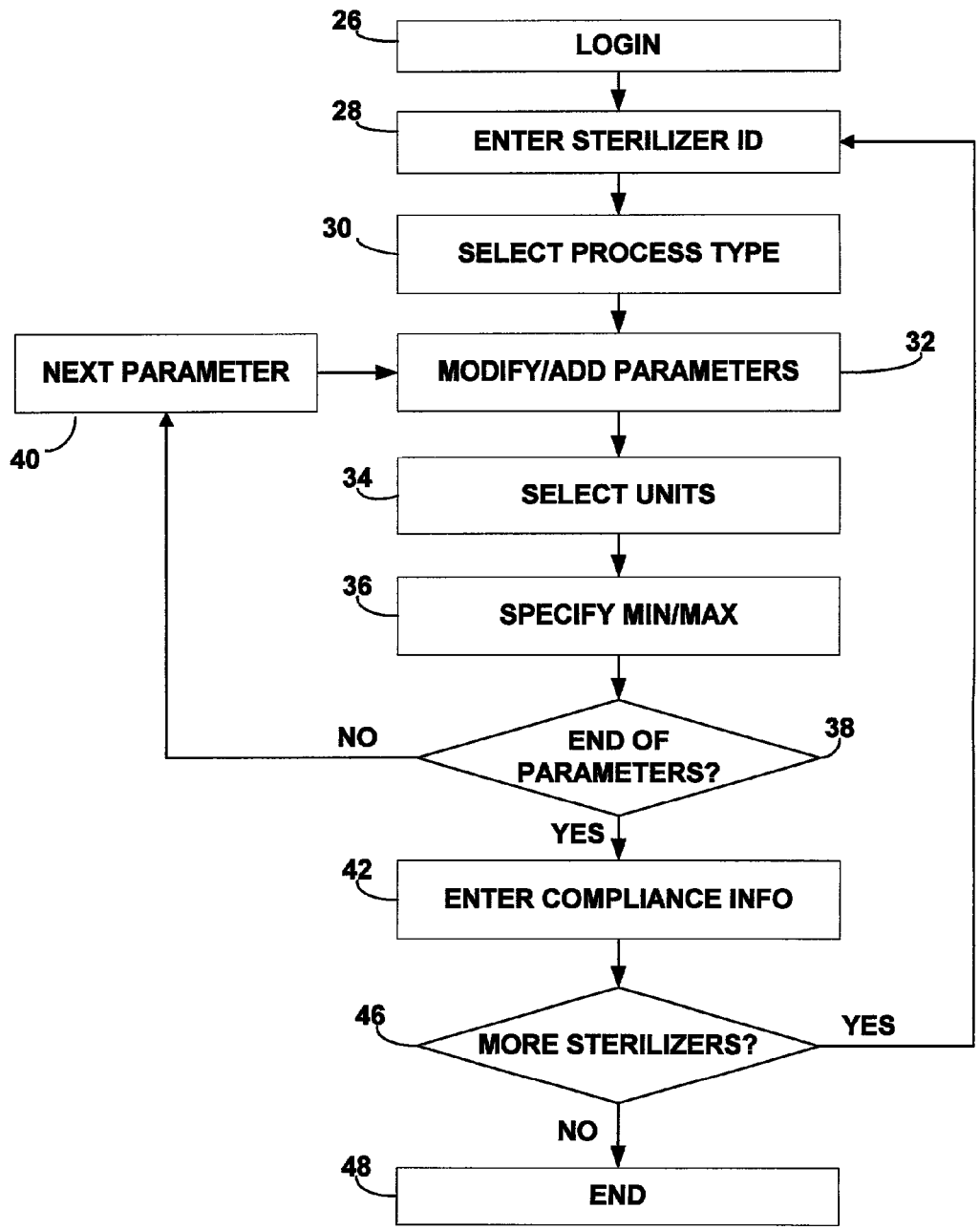
FIG. 5 is a flow diagram illustrating a process for customization of information for sterilizers.

FIG. 5 is a flow diagram illustrating customization of information for one or more sterilizers. In some embodiments, the process may be carried according to the order of the tabs from left to right in the user interface screen of FIG. 4, i.e., sterilizers, monitor settings, destinations, load items, users and permissions. The sequence permits the user to first create an ID code for a particular sterilizer, and then customize the sterilizer according to logical progression of attributes of the sterilizer.

Following system login (26), to customize system 10, the user may select a "customize" option from a dropdown menu in a toolbar presented on display device 16. Then, the user may setup a list of sterilizers within the facility. This capability may be limited to particular users. Accordingly, if a user does not have permission to setup the sterilizer list, the sterilizers tab may be "grayed out." Also, the sterilizers box on the left of the customization window may initially be empty. In this case, the user may select an "add" button from the customization window, permitting an authorized user to submit a new sterilizer to the list. An authorized user also may change the ID code for a sterilizer or delete a sterilizer from the list.

As shown in FIG. 5, to setup or modify the sterilizer list, a user may enter an identification (ID) code via user input device 14 for a particular sterilizer within the sterilization facility (28). The ID code may be a number, as indicated in FIGS. 2 and 3 above, an alphanumeric name, or simply a alphabetical name. Once the sterilizer is entered, the user may click the pertinent ID code to highlight the sterilizer for further customization.

Figure 6:
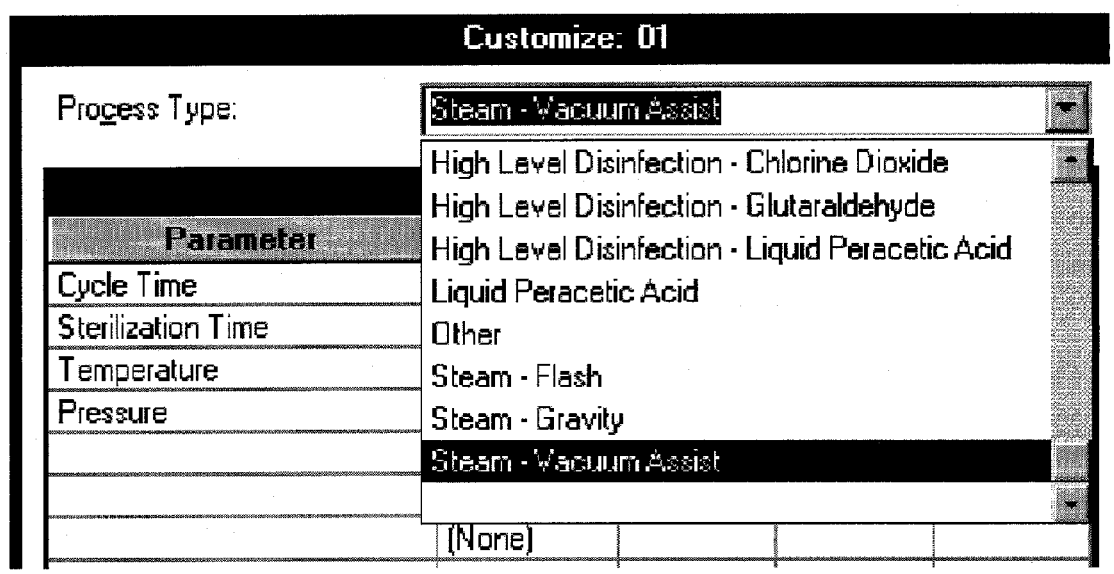
FIG. 6 illustrates an example user interface screen presenting customization of information for sterilization process types.

FIG. 6 illustrates an exemplary process type and parameter customization window for sterilizer "01." The user selects a process type (30) for the sterilizer. The user may select the process type from a drop-down list, pick list, or other selection medium presented by display device 16 under control of processor 12, as illustrated in FIG. 6. The process type may be, for example, steam- with vacuum assist, steam- with gravity, steam- with flash, ethylene oxide, H202/gas plasma, liquid peracetic acid, or high level disinfection (chlorine dioxide, glutaraldehyde, liquid peracetic acid, and the like).

Upon selecting the process type applicable to the sterilizer, the user may modify or add process parameters (32) that define the process range for the sterilizer. The process parameters for the selected process type may appear below the process type field within the user interface screen illustrated in FIG. 4. In particular, a process parameters box, as shown in FIG. 4, may present a number of default parameters. The user may specify units (34) for the parameters, as well as minimum and maximum values (36) for each parameter. FIG. 7 illustrates presentation of parameters within an exemplary process type and parameter customization window for sterilizer "01."

For example, the user may highlight a set of units or a value with a pointing device, and then modify the units or value. For the units, a drop-down menu of different units may be presented when the units are selected. FIG. 8 illustrates presentation of drop-down menu feature for selection of particular units. The minimum and maximum values may serve to define an acceptable operating range for the parameters. If a parameter value entered by a user during later recordation of a sterilization process falls outside of the operating range specified by the minimum and maximum values, the corresponding load record may be flagged for inspection.

If the user has not reached the end of the parameters (38) desired for the sterilizer, the process continues and the user enters the next parameter (40). When the user is finished entering and defining parameters (38), the user may be prompted to enter identification information for the sterilizer. For example, the identification information may include the make, model and serial number of the sterilizer, providing necessary sterilizer identification information for compliance requirements. The user continues the process until information has been entered for all of the desired sterilizers (46, 48).

Figure 9:
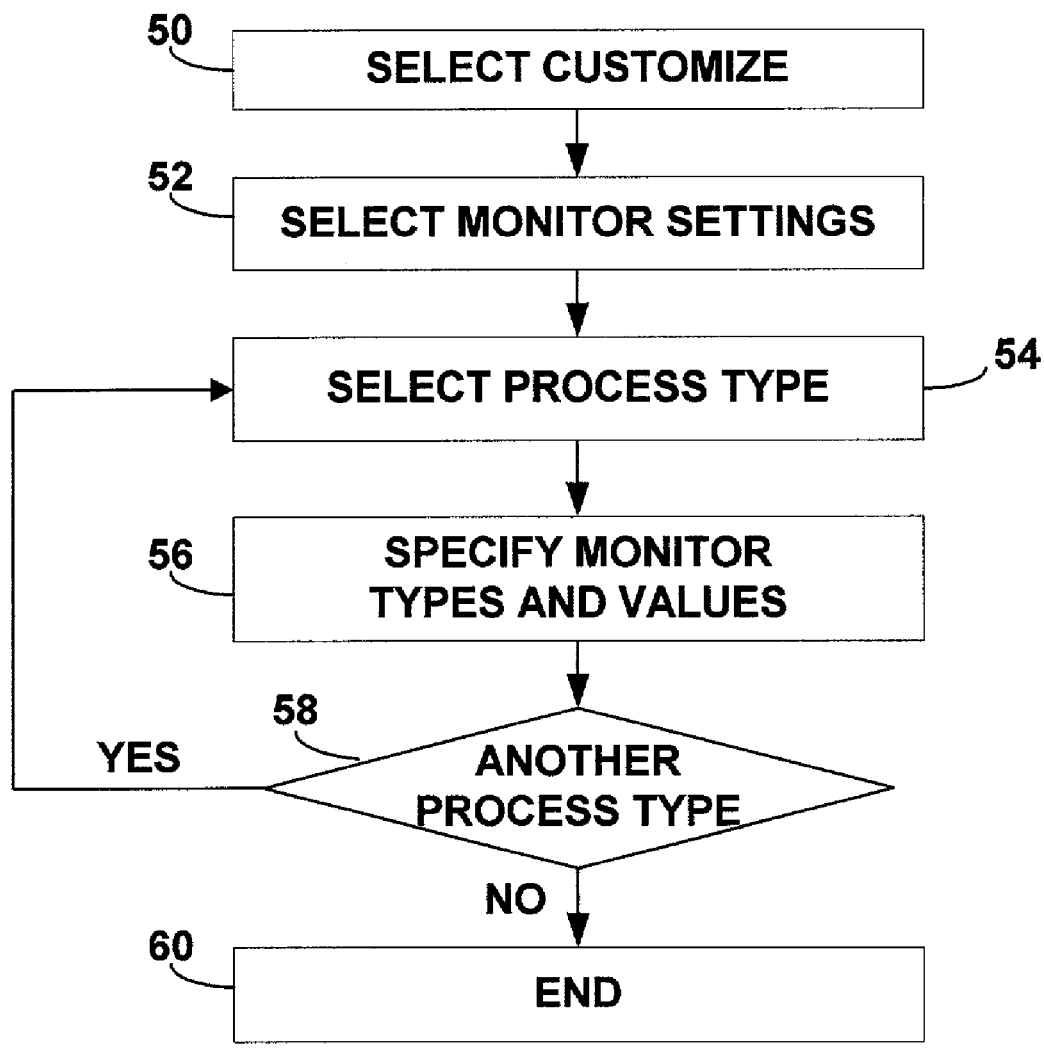
FIG. 9 is a flow diagram illustrating customization of monitor settings.

FIG. 9 is a flow diagram illustrating configuration of information for sterilization process types. Upon selection of customize option (50), followed by selection of the monitor settings tab (52), the user selects the applicable process type (54) for a sterilizer. The user specifies the monitor types applicable to the process type, e.g., biological, chemical, Bowie-Dick type test, and the pertinent values for the monitor type (56). Upon completing the monitor settings for a particular process type, the user moves on to the next process type (58) and continues until all or a desired set of the process types have been completed (60).

Figure 10:
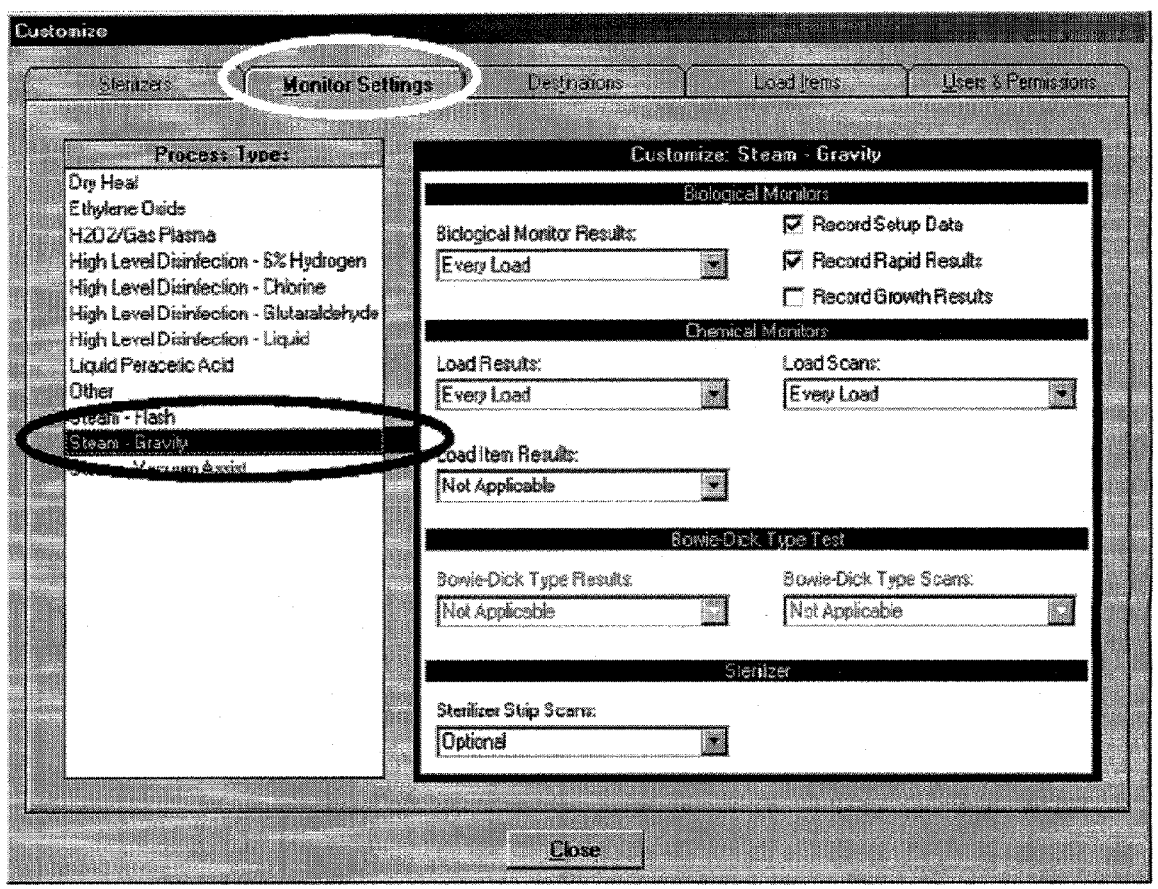
FIG. 10 illustrates an example user interface screen presenting customization of monitor settings.

FIG. 10 illustrates an example user interface screen presenting customization of information for sterilization process types. In operation, the user selects one of the process types, e.g., by highlighting a process type in the process type list with a pointing device. In response to the selection, processor 12 drives display device 16 to present a "Customize" window for the process type. With reference to the example of FIG. 10, if the "Steam—Gravity" process type is selected, the "Customize: Steam—Gravity" window is displayed. Within the "Customize: Steam—Gravity" window, the user interface screen presents a number of different monitor types and provides input media for selection of data associated with the monitor types.

For biological monitors, for example, the "Customize: Steam—Gravity" window provides a drop down menu to specify whether the biological monitor results should be run for every load sterilized via the selected process type, or whether the results may be run periodically. Also, the scope of result reporting may be selected ("Record Setup Data," "Record Rapid Results," "Record Growth Results"), e.g., via checkboxes. The selected values determine what will be displayed on the "biological" tab of the load records produced for the selected process type.

Similarly, for chemical monitors, the user interface screen may permit selection of the load results, load scans, and load item results generated of the process type in the "Customize: Steam—Gravity" window. The value may pertain to any internal or external chemical monitors for which the user may choose to keep a permanent record, including load record cards. The selected values will determine what will be displayed on the "chemical" tab of the load records for the selected process type.

In the example of FIG. 10, the Bowie-Dick Type Test area is grayed out, indicating this type of monitor is not applicable to the selected process type, i.e., "Steam—Gravity." The "Customize: Steam—Gravity" window may permit selection of values for "Sterilizer Strip Scans" for the selected process type. The selected values will determine whether sterilizer strip scans will be required, optional or not applicable within the facility for the selected process type, and will govern the contents of the sterilization tab of load records created for the process type.

Figure 11:
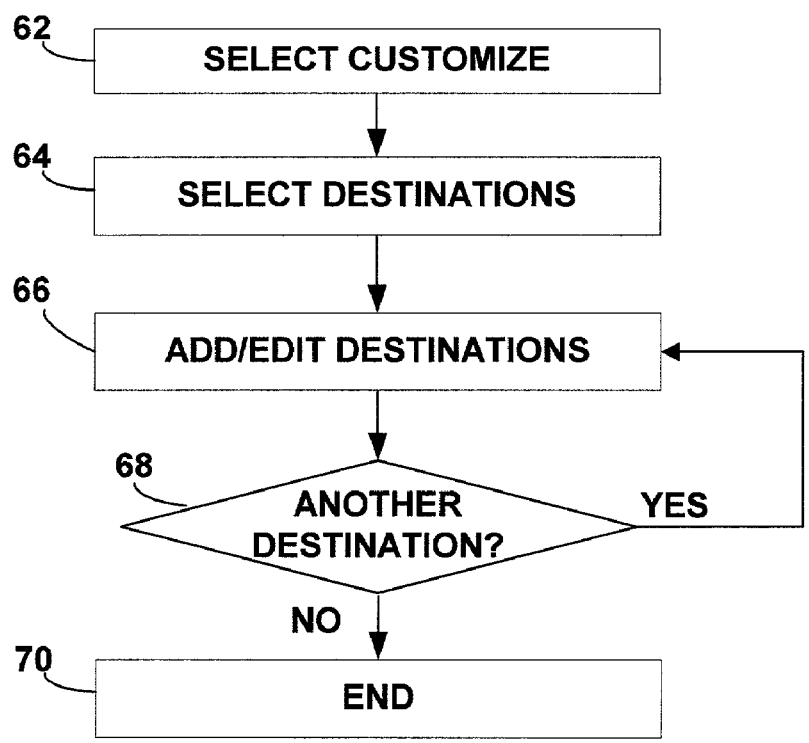
FIG. 11 is a flow diagram illustrating customization of destinations.

FIG. 11 is a flow diagram illustrating configuration of information for sterilized load destinations. As shown in FIG. 11, upon selecting customize (62), the user may select particular destinations served by the sterilization facility or department (64). In particular, the destinations may be locations to which the sterilization facility or department sends processed load items. The user may add new destinations, or edit information for existing destinations (66). The user may delete destinations from the list of destinations for the sterilization facility or department. The process continues until the user has added, edited, or deleted all desired destinations (68, 70). Destinations entered during the customization process may appear in a drop-down list for selection by a user when creating a load record or other recordkeeping.

Figure 12:
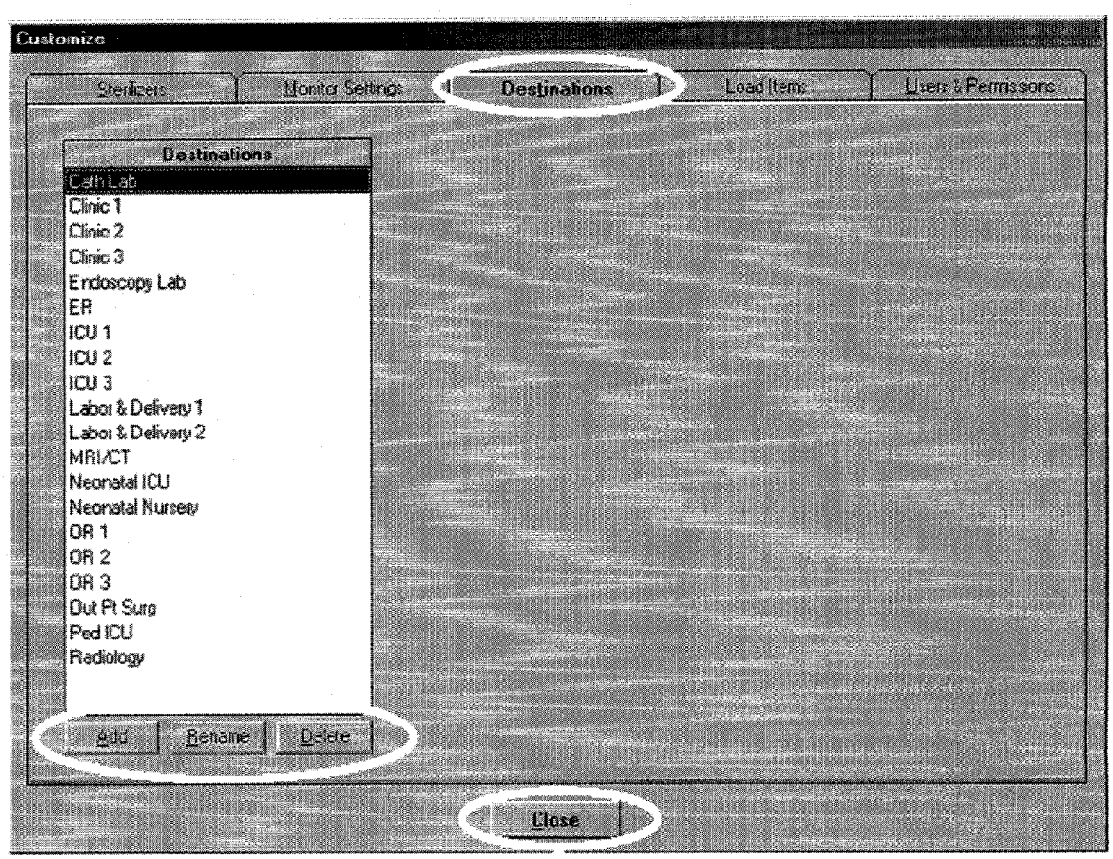
FIG. 12 illustrates an example user interface screen presenting customization of destinations.

FIG. 12 illustrates an example user interface screen for use in editing sterilized load destinations as described with reference to FIG. 11. As shown in FIG. 12, upon selection of the "Destinations" tab (circled) in the customization window, a user may view a list of destinations. Each destination has an ID code, which may take the form of a name of a destination such as "Cath Lab," "Clinic 1," "Endoscopy Lab," "OR 1," "Radiology" or the like. The user may select the "Add," "Rename" or "Delete" button (circled) to modify the list. When a second "Labor & Delivery" room becomes a client of the sterilization department, for example, it may be desirable to rename an existing facility as "Labor & Delivery 1" and the new department as "Labor & Delivery 2." In this case, the user may highlight a particular destination and then click the "Rename" button in order to rename the destination. The "Destinations" tab in the customization window may be grayed out if the present user is not authorized to edit destinations.

Figure 13:
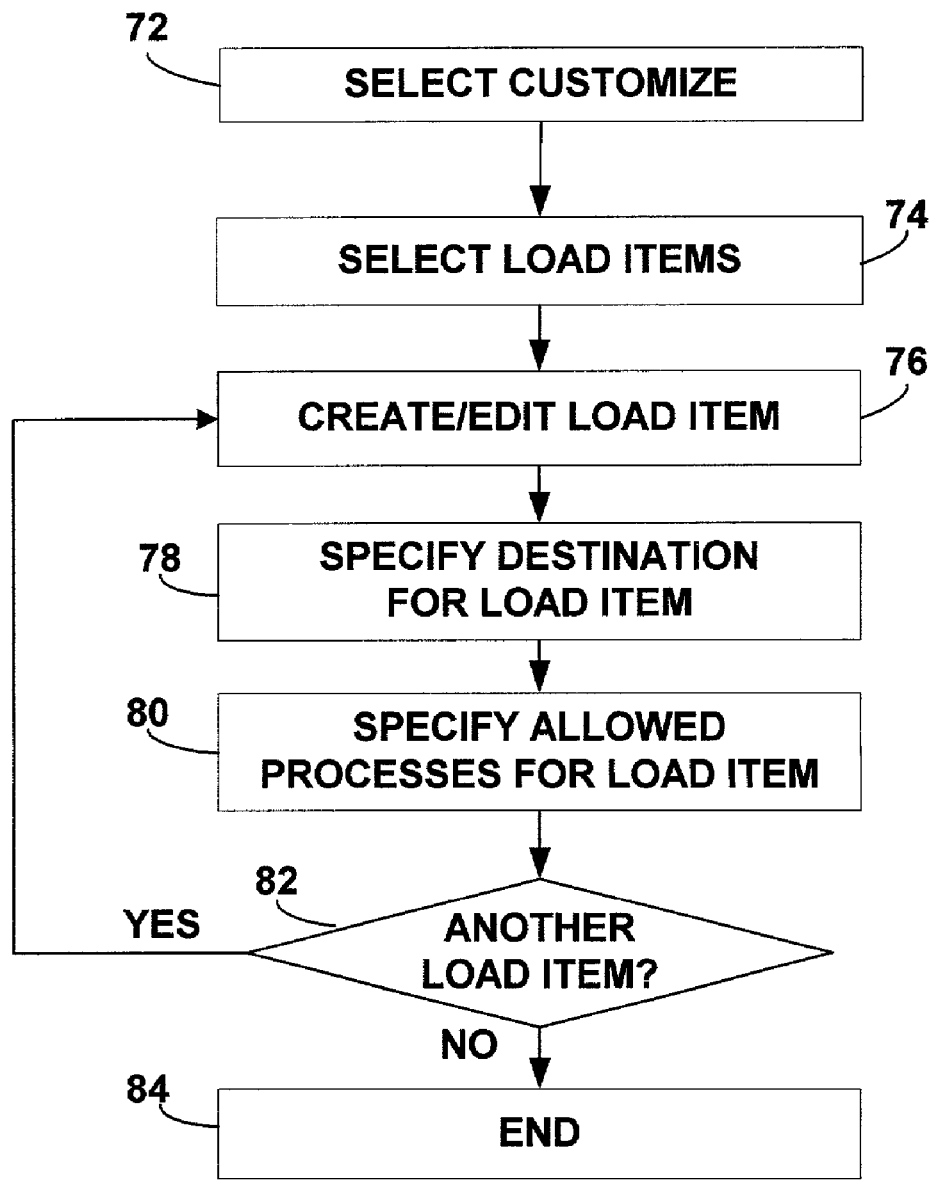
FIG. 13 is a flow diagram illustrating customization of information for sterilized load items.

FIG. 13 is a flow diagram illustrating configuration of information for a new load item. In other words, the process illustrated in FIG. 13 depicts set up of sterilization records for load items within system 10. This feature may allow a user to create a list of load items, or import an existing list of load items. In addition, the user may be able to set default destinations for a load item, link load items to other data such as a pick list, a picture of the load item or other files, add special instructions or notes for a load item, identify load item destinations, and designate allowed sterilizer or disinfection processes and biological monitoring requirements for each item.

As shown in FIG. 13, upon selection of the customize option (72), the user selects the load items tab (74). The user then creates or edits a load item (76) and designates a destination for the load item (78). Alternatively, the user may delete an existing load item. Upon specification of allowed processes for a particular load item (80), the user may continue to process other desired load items (82) or end the process (84). With this process, the user can create a list of all load items processed within the sterilization facility or department.

Figure 14:
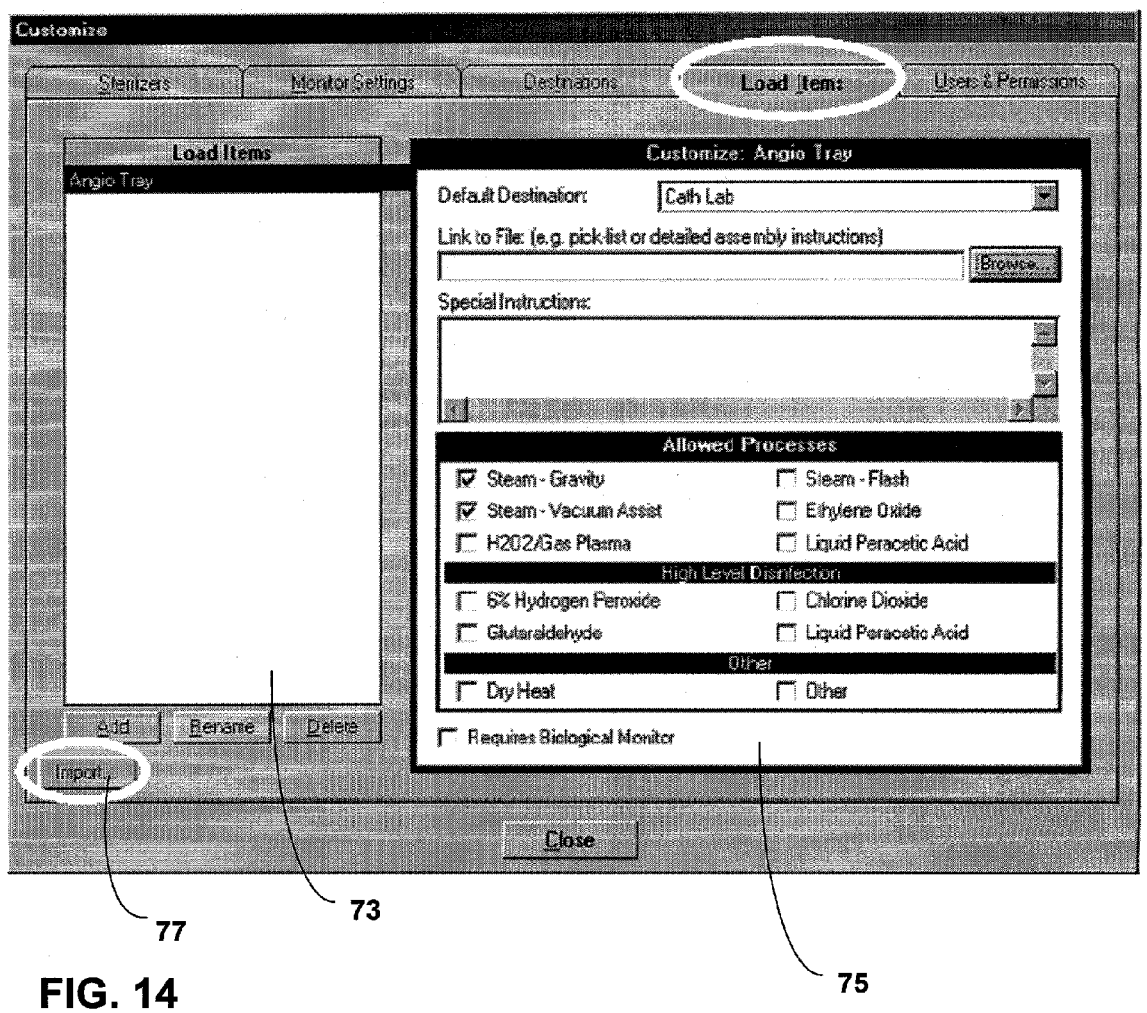
FIG. 14 illustrates an example user interface screen presenting customization of load items.

FIG. 14 illustrates an example user interface screen for customization of information for load items. As shown in FIG. 4, a load item window displays a list 73 of load items and a load item customization window 75. In example load item list 75 of FIG. 14, one load item ("Angio Tray") is listed. The user may add, rename, or delete listed load items. Also, an "import" button 77 (circled) that permits the user to import load item and accompanying information from another file. Load item customization window 75 presents a variety of information for a selected load item ("Angio Tray").

For example, load item customization window 75 may present a default destination with a drop-down list to select other locations, a link to a file with information pertaining to the load item, a special instructions field that records notes or advice about processing of the load item. The linked file may contain, for example, a surgeon preference or "pick" list, a tray contents list, a picture of load item contents, or detailed assembly instructions. The linked file may be selected, for example, using the "Browse" button in load item customization window 75.

In addition, as shown in FIG. 14, load item customization window 75 may include checklists for selection of allowed sterilization processes, high level disinfection processes, or other processes that can be used with the load item. In the example of FIG. 14, the users makes selections to indicate that the load item requires steam—gravity processing or steam—vacuum assistor steam—flash processing. If the load item is later used with a non-allowed process, and a user enters load item information documenting that process, system 10 may present a message indicating that the load item is not designated to run with the current process. The user then may override the message or run the load item with one of the allowed processes.

Figure 15:
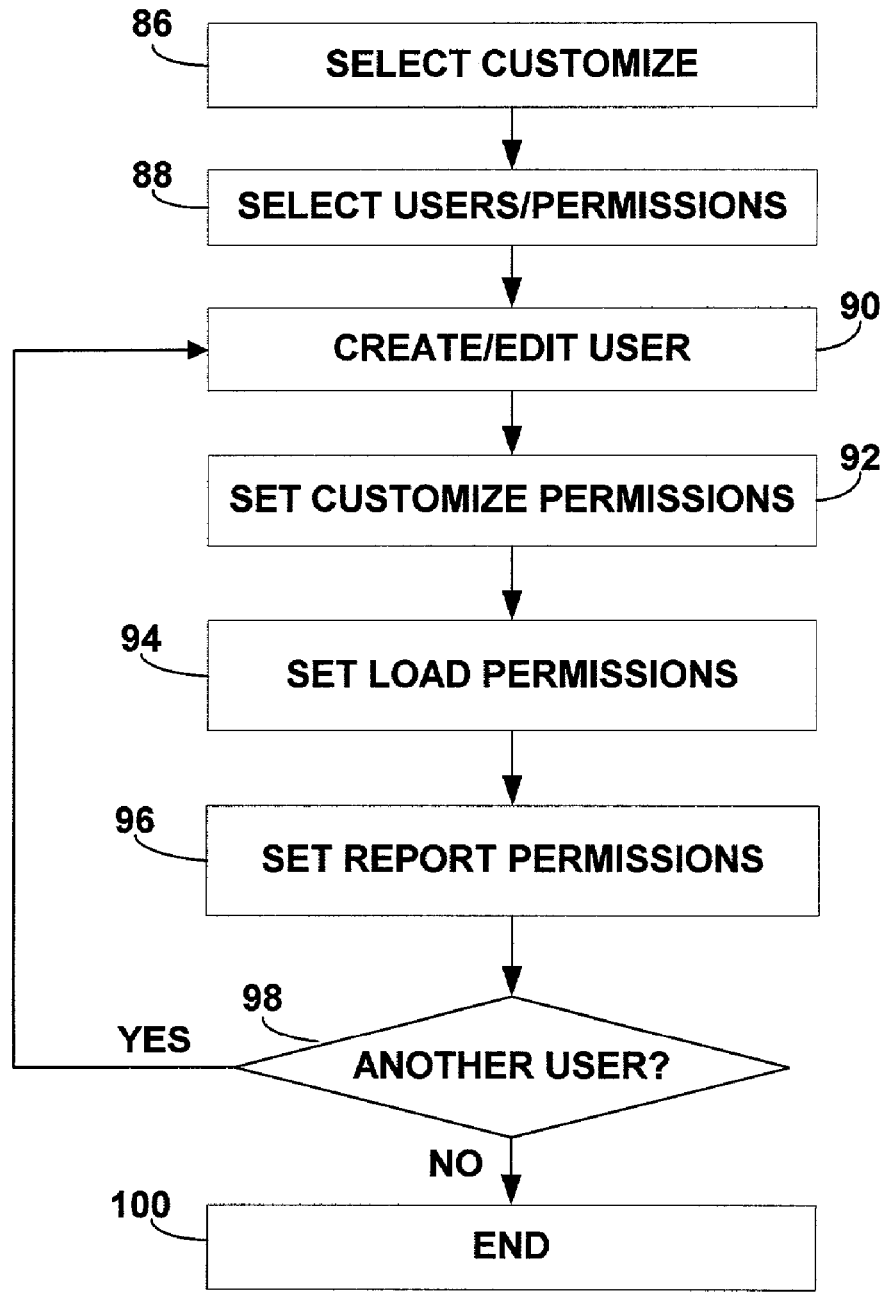
FIG. 15 is a flow diagram illustrating configuration of user accounts.

FIG. 15 is a flow diagram illustrating configuration of permissions for users in the system of FIG. 1. As shown in FIG. 15, upon selection of the customize option (86), an administrator selects the users/permissions tab (88). The administrator then may create a new user account or edit an existing user account (92). Also, the administrator may delete existing users. In each case, the administrator responsible for creating, editing or deleting a user should be a person assigned a high level of authorization, such as a sterile processing supervisor or an information technology (IT) system administrator for the sterilization facility.

The administrator may set permissions for different categories of modification. In particular, the administrator may set customize permissions that specify the level of permission assigned to a user for use of the "customize" option (92). In addition, the administrator may set load permissions (94) that specify the level of authorization for a user to create and process loads. The administrator also may set report permissions (96) that specify whether a user may generate reports from sterilization records and search the sterilization records. The administrator continues the process for a group of users (98) until permissions have been set for all desired users, and the administrator ends the process (100). In some embodiments, a default set of permissions may be provided for each user. In this case, the administrator need only modify the default permissions to reflect a desired set of permissions for individual users.

Figure 16:
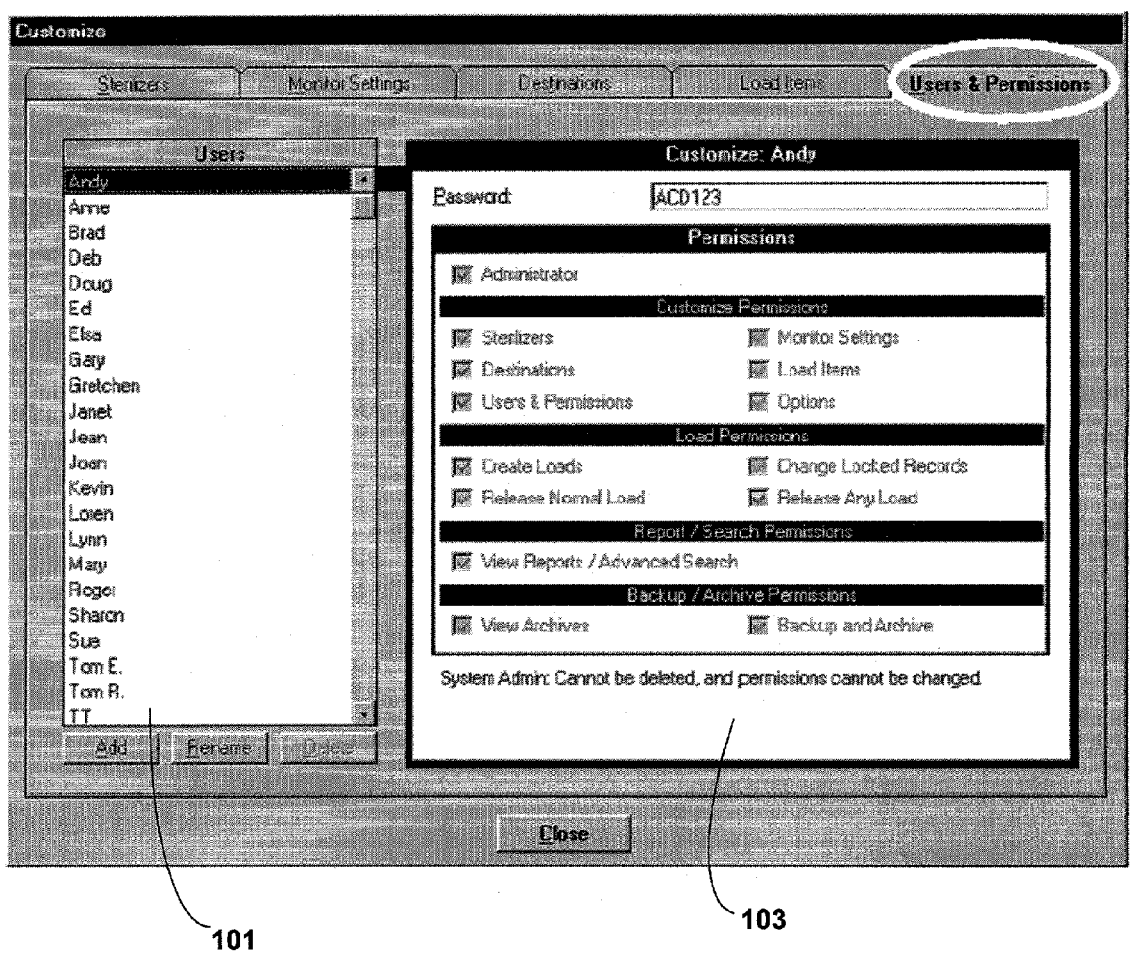
FIG. 16 illustrates an example user interface screen presenting configuration of user accounts.

FIG. 16 illustrates an example user interface screen for customization of information for users and user permissions according to the process outlined in FIG. 15. The user interface screen of FIG. 16 may include a list of users 101 and a user customization window 103. An administrator may add, rename or delete users in user list 101. By highlighting one of the users, the administrator may access the permission settings for a user via user customization window 103. User customization window 103 may permit the administrator to set a password for a user, and designate a user as an administrator or non-administrator. In the example of FIG. 16, the "Administrator" box is checked, indicating that the user named "Andy" has administrator-level permissions.

In addition, the administrator may check boxes to specify which customize permissions are assigned to the user, e.g., permission to modify information in the customize categories: sterilizers, monitor settings, destinations, load items, users and permissions, and options. The options category, not previously discussed above, may pertain to a setup/options selection on the customization window toolbar (FIG. 4) or reporting window (FIG. 2) that permits customization sterilization monitor formats.

In user customization window 103, the administrator also may set permissions for load activities such as create loads, change locked sterilization records for loads, release normal loads, and release any load. The create loads activity permits a user to create new loads and sign off on load record data. The release normal load activity permits the user to set the load "status" to "released" for load records that are not designated as "flagged records," e.g., load records that do not contain out-of-range process parameter values. The change locked record activity may permit a user to unlock existing sterilization records and make changes. The release any load activity permits the user to set the load "status" to "released" for any load, whether the load is normal or flagged. For flagged loads, it may be desirable to restrict change permissions to supervisors, administrators or other persons with higher authorization levels.

As further indicated in user customization window 103, the administrator also may set report and search permissions for a user to allow the user to access reports and perform advanced searches. Also, the administrator may set backup and archive permissions for individual users. In particular, only certain users may be permitted to view archived sterilization records. In addition, the administrator may restrict the ability of users to backup files, restore files or archive files containing or associated with sterilization records.

In general, the ability to set permissions can significantly improve the integrity of the sterilization records maintained by system 10, and protect the sterilization records against intentional corruption or inadvertent corruption, especially in comparison to paper records. For example, authorization to create, modify or access the electronic sterilization records may be restricted by selectively granting different levels of permission to particular users based on levels of confidence, training, or scope of responsibility. Data integrity may be very important in a subsequent quality review or audit of the sterilization records.

Figure 17:
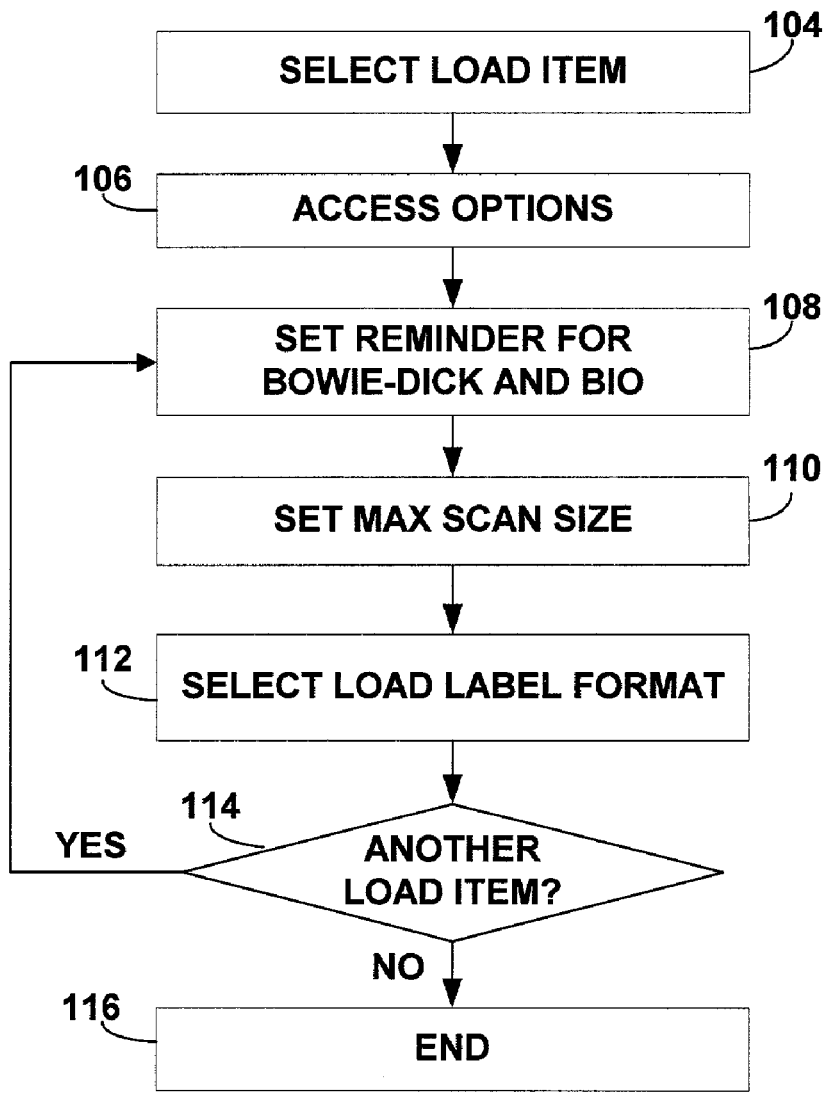
FIG. 17 is a flow diagram illustrating configuration of scanning and label options.

FIG. 17 is a flow diagram illustrating configuration of sterilized load item recording options. As shown in FIG. 17, a user may select a particular load item (104) in the reporting window (FIG. 2) or the customization window (FIG. 4), and then access "options" in the window toolbar (106). The user then may set a reminder for Bowie-Dick type tests and biological monitors used with the selected load item (108). In addition, the user sets a maximum scan size (110) reflecting the scan size applicable to Bowie-Dick type tests, chemical monitors, and sterilizer strips. The user also may select or otherwise specify a load identification label format (112) that defines the layout of load identification label information such as date, month, and year. Upon setting options for a desired number of load items (114), the process ends (116).

Figure 18:
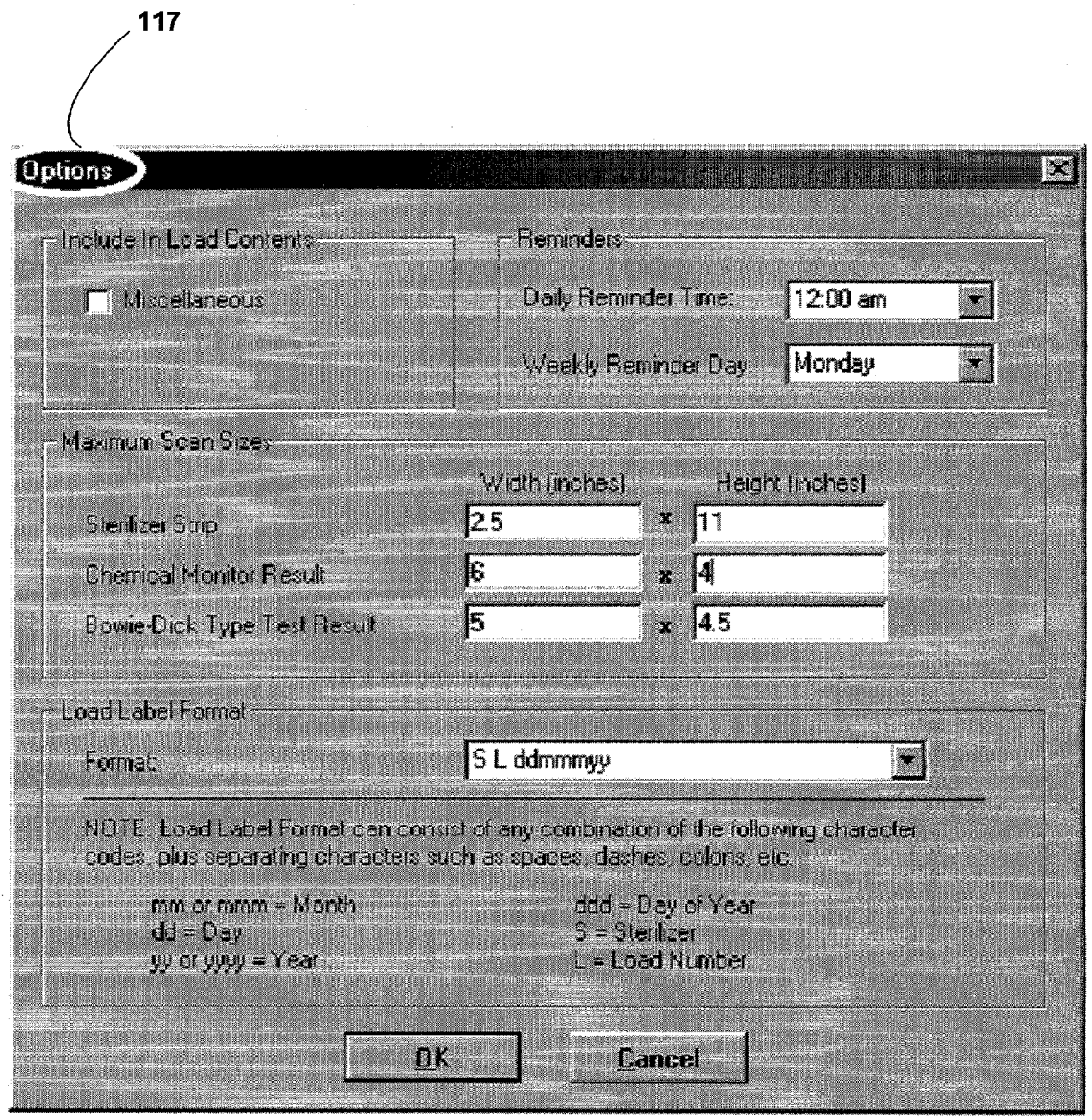
FIG. 18 illustrates an example user interface screen presenting configuration of scanning and label options.

FIG. 18 illustrates an example user interface screen for customization of sterilization monitor information. The user interface screen of FIG. 18 provides an options window 117 that includes a reminders field. The reminders field enables the user to specify a daily reminder time or a weekly reminder day for display of a reminder message by system 10. The time or day are selected if the user previously selected "daily" or "weekly" settings in the monitor settings tab of the customization window (FIG. 4). At the specified time or day, processor 12 causes display device 16 to present a message reminding the user to run the applicable Bowie-Dick type test or biological monitor for the selected load item.

The options window also may include text entry boxes for a user to enter maximum scan sizes. The text entry boxes may initially present default scan sizes for each category of monitor, including sterilizer strips, chemical monitor results, and Bowie-Dick type test results. The scan sizes may be expressed in terms of a width and height. The scan sizes can be customized to reflect the scan sizes necessary for tests and strips used at the particular sterilization facility. In addition, as shown in FIG. 18, the options window may present a drop-down menu that permits a user to select a load label format.

Figure 19:
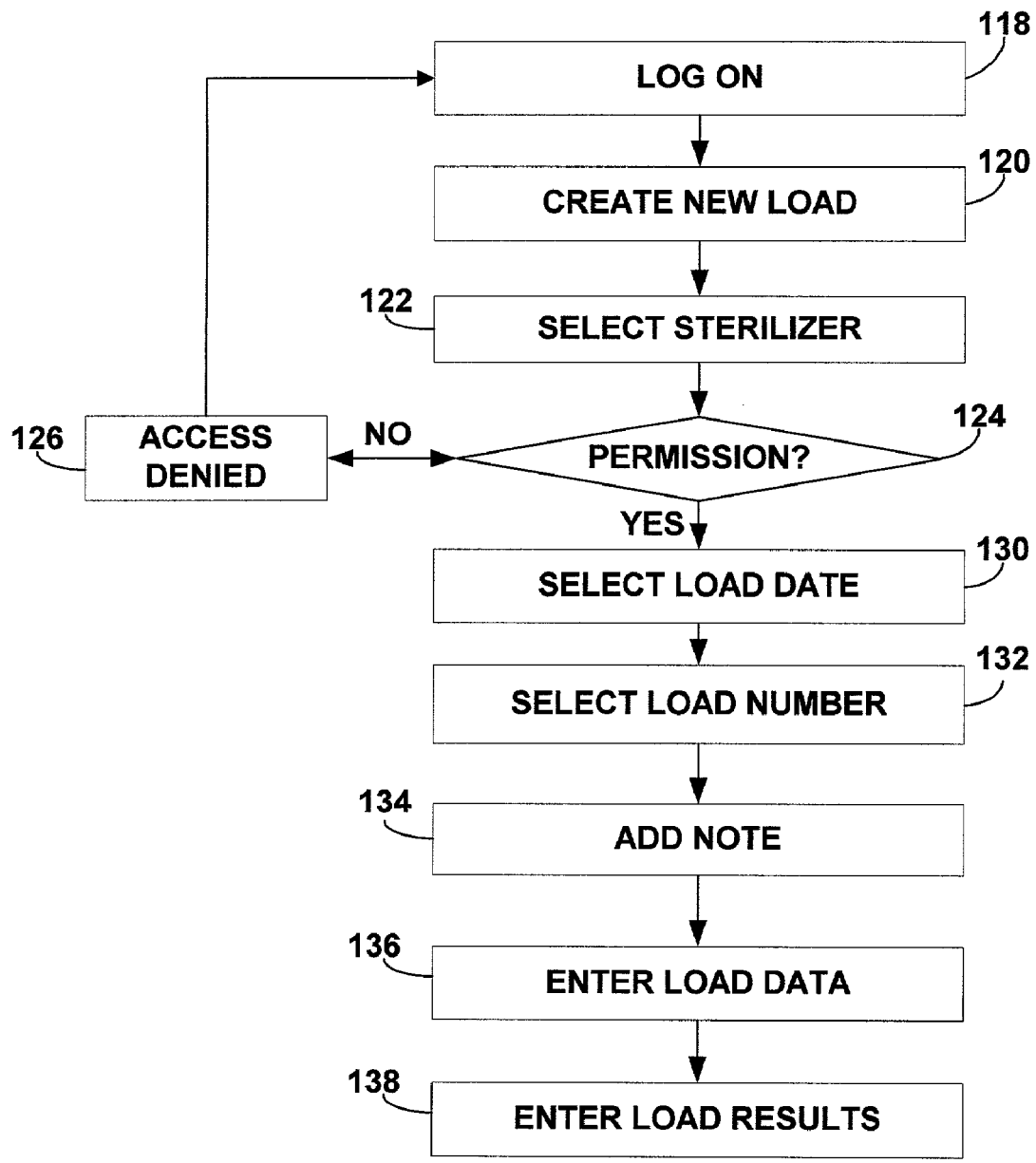
FIG. 19 is a flow diagram illustrating creation of a sterilization record for a new load.

FIG. 19 is a flow diagram illustrating creation of a sterilization record for a new load and entering data for the load. As shown in FIG. 19, a user first logs on to system 10 (118). Upon selecting the toolbar option to create a new load (120), the user selects a sterilizer to process the new load (112). Processor 12 then determines whether the user has permission to create a new load for the sterilizer (124). If not, processor 12 drives display device 16 to present a message indicating that access is denied (126), and may then revert to log on (118).

If the user has sufficient permission (124), the user is permitted to continue. The user then selects a date for the load (130) and a load number (132). The default load date may be today's date. System 10 may present the next available load number for selection by a user. However, the user may override the load number and select a chosen load number. If the load number is already in use, system 10 generates a message to that effect. Upon entry of a valid load date and load number, system 10 may present a load record window. The user may have the option of adding a note to the load record (134). For example, the user may select an "add note" command from the load record window toolbar, and attach information to the load. The note may appear within a history tab associated with the load record, and be accessible by subsequent users.

As further illustrated in FIG. 19, the user enters load data (136) and specifies load results (138) applicable to the load. The load record may include a load contents field, in which the user may enter data concerning the quantity of load items, a description of the load item, the applicable destination. The user also may enter the type of results (138) that should be provided for the load. For example, the user may check boxes present by the load record window to indicate whether load results for biological, chemical, Bowie-Dick tests or a combination of those tests should be provided for the new load.

Figure 20:
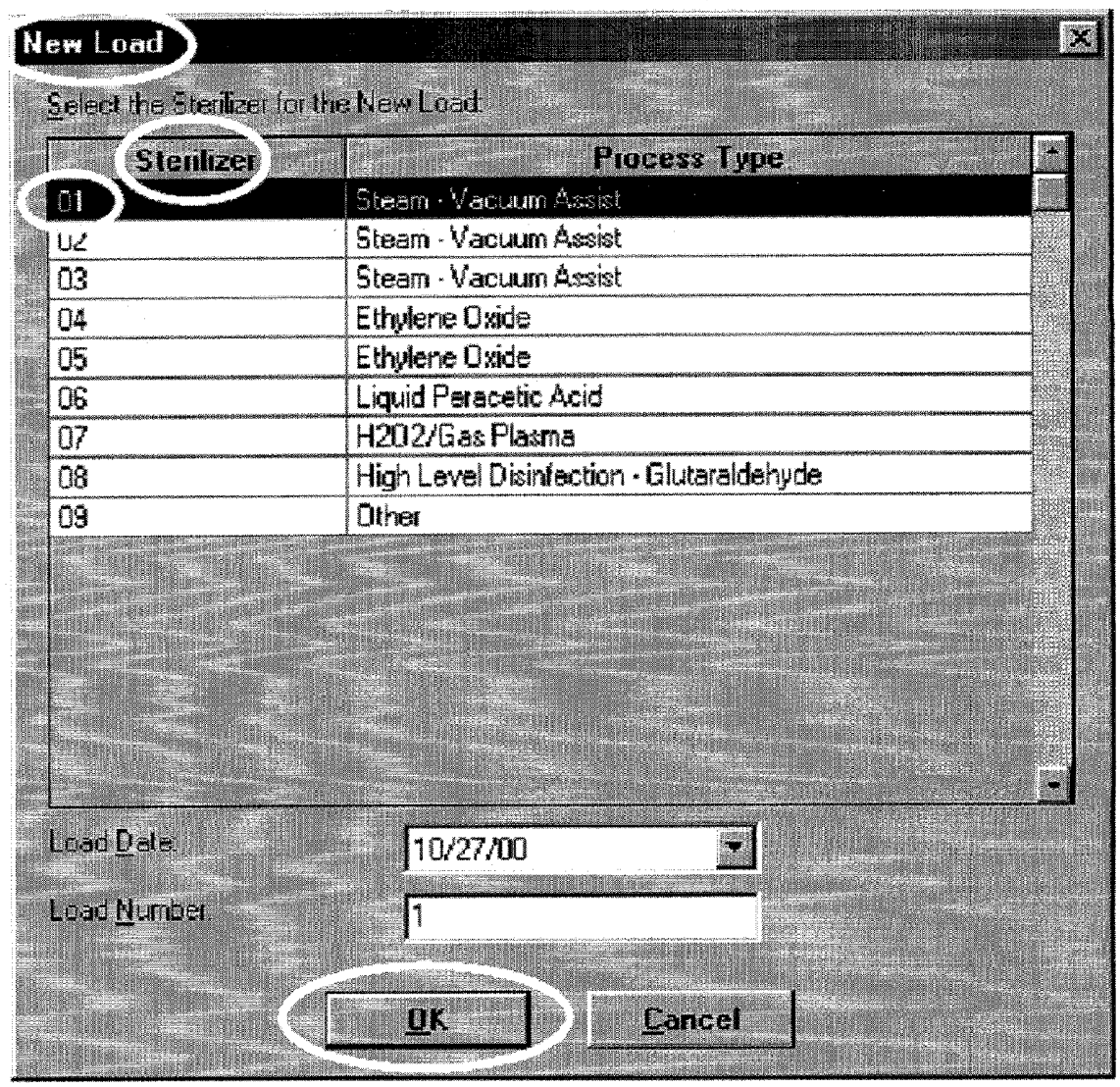
FIG. 20 illustrates an example user interface screen presenting information for creation of a sterilization record.

FIG. 20 illustrates an example user interface screen presenting a new load window for presentation to a user during creation of a new load. As shown in FIG. 20, a user may select a sterilizer for a new load (122) by highlighting one of the sterilizers listed in the new load window. By selection of one of the sterilizers, the user also specifies the process type for the load, i.e., the process type applicable to the selected sterilizer. In addition, the user may select the load data and load number (130, 132) within the new load window. For example, the load data may be selectable via a drop down list. As mentioned above, a default load date and load number may be initially displayed within the new load window.

Figure 21:
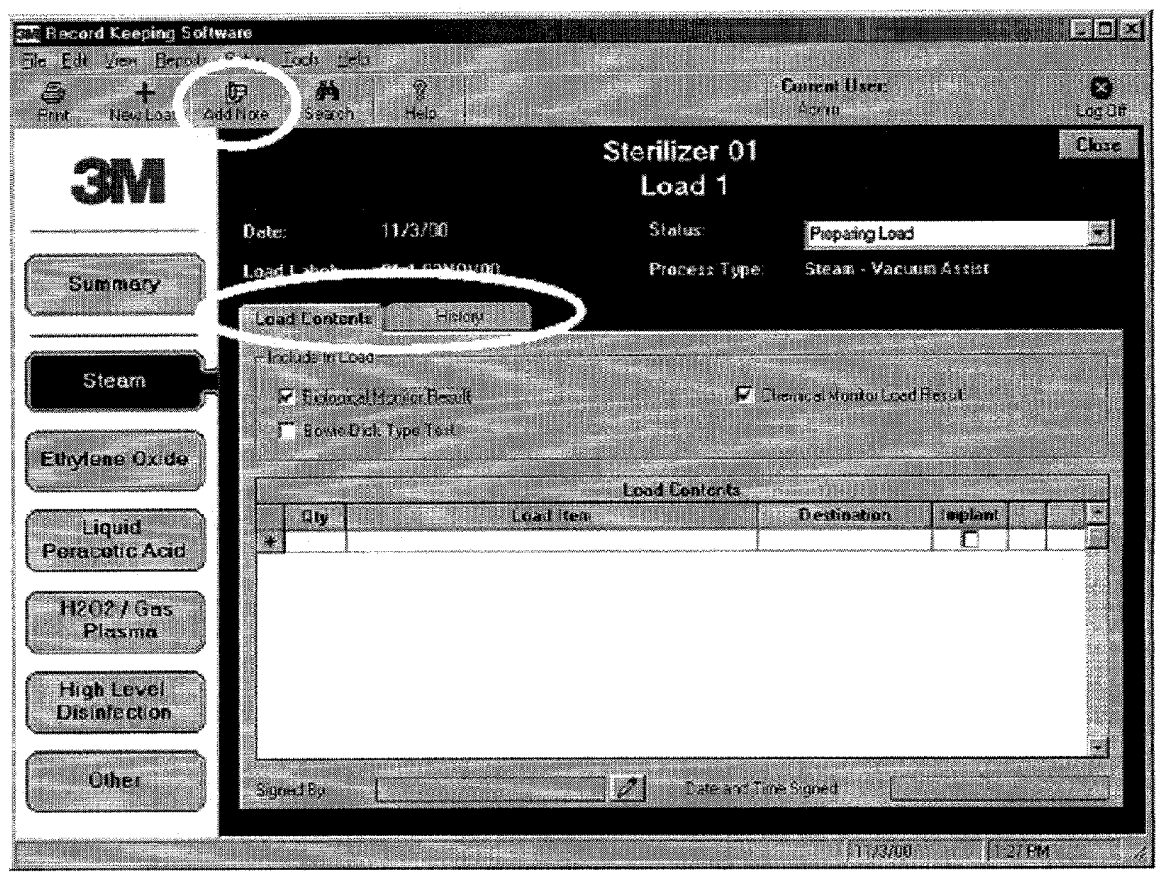
FIG. 21 illustrates an example user interface screen presenting an initial load record.

FIG. 21 illustrates an example user interface screen presenting an initial load record window for a new load created by a user. The load record window may present the selected sterilizer ID code, the load number, load date, load label, process type, and the present status of the load. The load status is initially "Preparing Load" during creation of a new load. As shown in FIG. 21, the load record window also may include a load contents window and a history window. The history window may include notes entered by a user or a hypertext link to a document containing such notes. The user checks the applicable boxes in the load contents window to specify desired load results for the load, and enters load item quantity, description, and destination where indicated. The load contents window also may include a check box to indicate whether the load items are implantable.

Upon completion of data entry, the user may "sign off" on the load contents, e.g., by clicking the pencil icon shown in FIG. 21. In response, system 10 enters the user's name in the "signed by" field of the load record window. In this case, system 10 may change the pencil icon to a padlock icon and indicate the date and time in the "Data and Time Signed" field. In this manner, system 10 may lock the load record against further changes and record the identity of the user that created the load record. If changes are necessary, the user that created the record, or some other user with sufficient permissions, may click on the padlock icon and reenter the load record to make edits.

Figure 22:
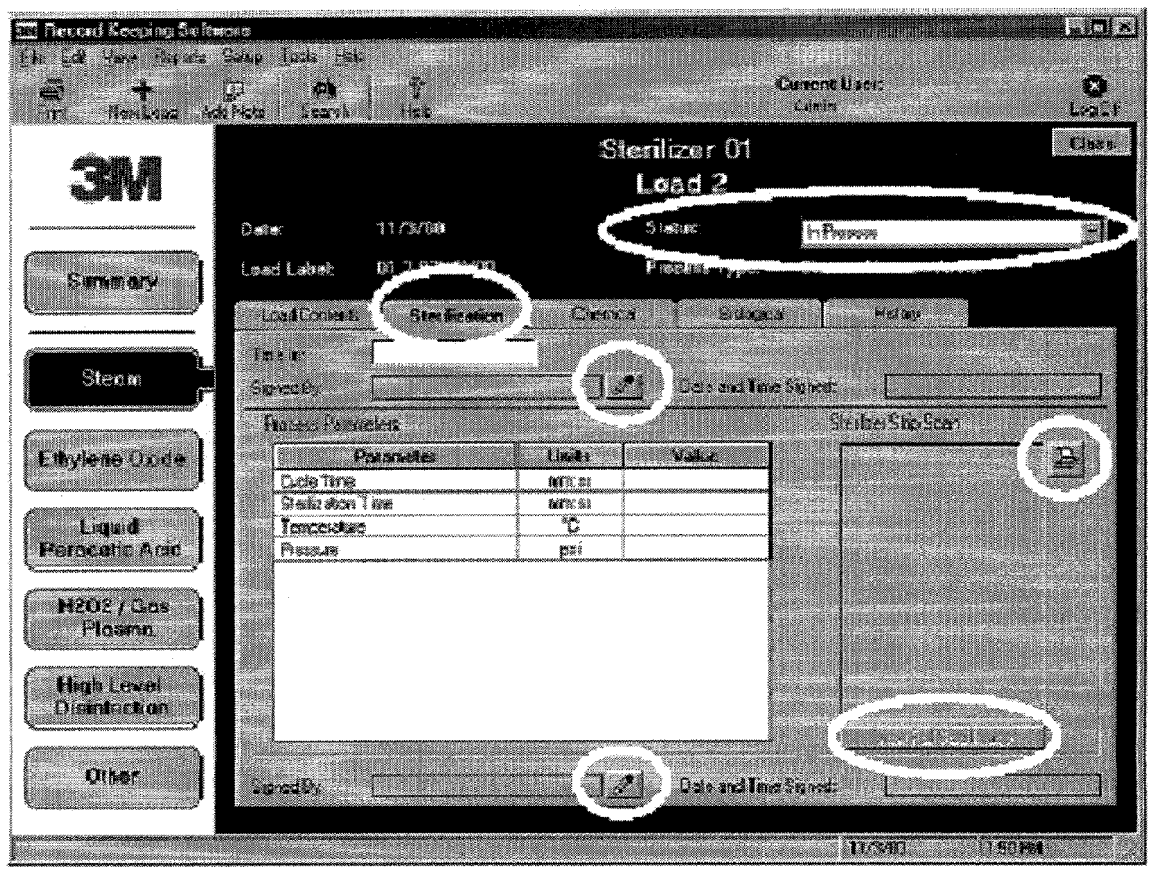
FIG. 22 illustrates an example user interface screen presenting a initial load record prepared for monitoring of a particular load.

FIG. 22 illustrates an example user interface screen presenting a load record window upon sign-off by a user. The load record window conforms substantially to the load record window of FIG. 21. Following sign-off, however, system 10 may present a new load record window that includes additional fields for the load based on the data entered by the user. If the user indicated that chemical monitor results should be recorded for the load, a chemical data field may appear. Likewise, a biological data field appears in the load record window if the user selected biological results.

For example, as shown in the example of FIG. 22, the load record window includes a load contents tab, a sterilization tab, a chemical tab, a biological tab and a history tab. The sterilization tab permits the user to record a sterilization process in the load record. Until the user "signs off" on the sterilization tab, the load status remains "In Process." Upon placing the new load in the sterilizer, the user clicks the "time in" field and enters the then-current time. The user then clicks the pencil icon beneath the time in field, and system 10 records the name of the user and the date and time of signature.

When sterilization of the load is complete, the user enters the process parameters under "Value," e.g., by clicking in the "Value" field. If a default value for a parameter was entered already for the sterilizer, the default value can be entered automatically. If a minimum or maximum value was entered for a parameter when the user set up the sterilizer, any data recorded outside of those values will result in marking the load record as a flagged record, e.g., by placing a red dot in the upper left corner of the load record window.

The load record of FIG. 22 also illustrates an area for inclusion of a scanned sterilizer strip ("Sterilizer Strip Scan"). System 10 may prompt a user to scan the sterilizer strip using image scanner 18 (FIG. 1). System 10 associates the digital image with the load record and stores the digital image in sterilization information archive 22 (FIG. 1). Also, system 10 presents a thumbnail, i.e., reduced resolution, image of the actual sterilizer strip that was evaluated by the user. The load record may provide an embedded hypertext link within the thumbnail image or, as shown in FIG. 22, a button ("View Full Size Image") that can be selected by the user to access the full resolution and full size version of the image.

Figure 23:
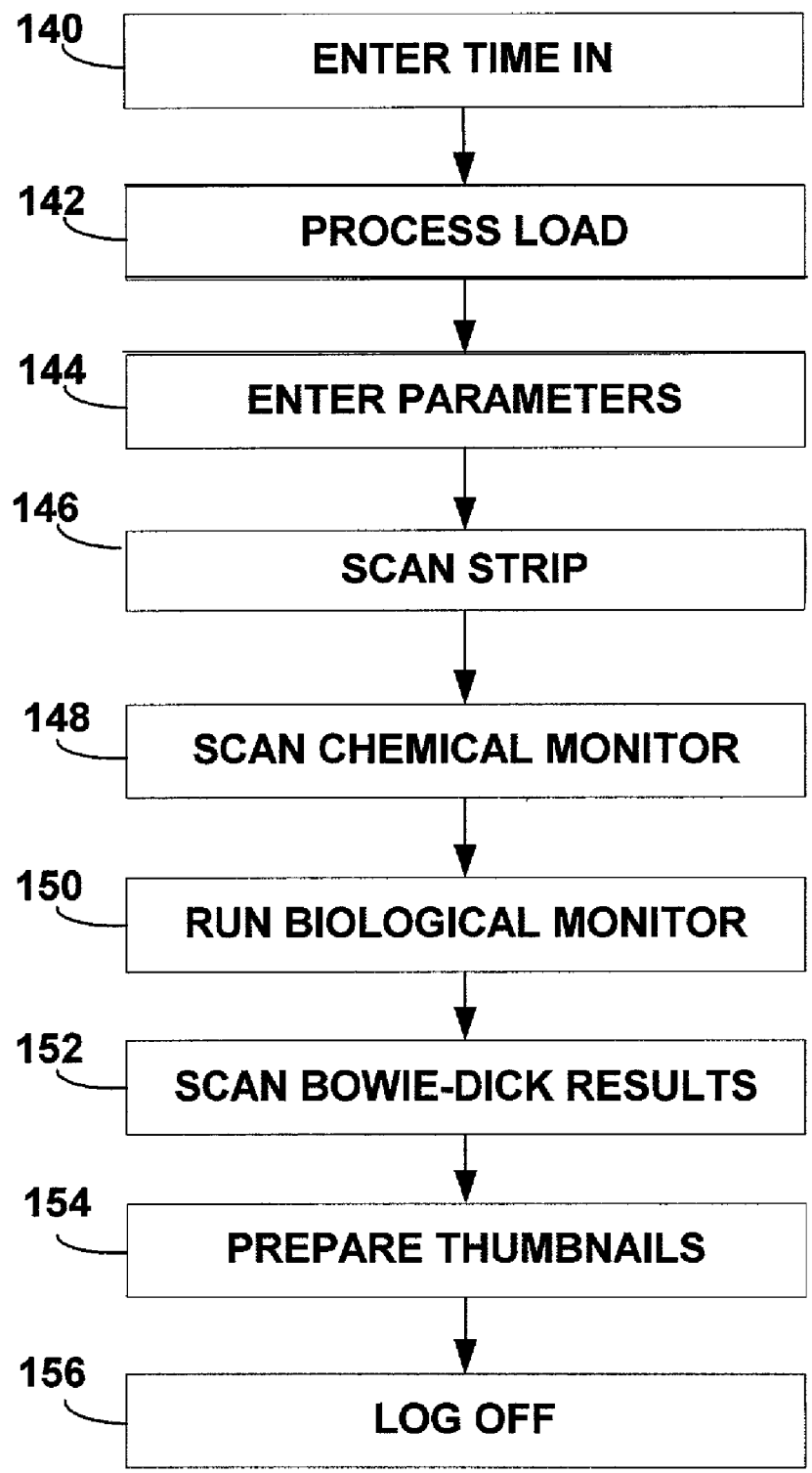
FIG. 23 is a flow diagram illustrating a process for entry of process information for a load.

FIG. 23 is a flow diagram illustrating entry of data into a sterilization record for a processed load. To process the load, the user enters into the load record a "time in," or time the load was submitted to a sterilizer for processing (140). Upon processing the load (142), the user enters parameter values into the load indicating the process values from the sterilizer (144). The user than may be prompted by system 10 to scan a sterilizer strip carried by the load using image scanner 18, as mentioned above. Image scanner 18 (FIG. 1) produces a digital image of the sterilizer strip that is stored in sterilization information archive 22.

Depending on the monitor settings entered by the user, the user also may be prompted to scan chemical monitor (148), run a biological monitor (150) and/or scan Bowie Dick type test results (152). Again, image scanner 18 scans the chemical monitor or the Bowie Dick test results to produce a digital image that is associated with the pertinent load record and stored in sterilization information archive 22. System 10 then may prepare "thumbnail" images of the scanned digital images (154) prior to user log-off (156).

The thumbnail images may be reduced resolution versions of the scanned digital images. For example, the thumbnail images may be stored in sterilization information archive 22 and associated with a particular load record. When the load record is retrieved for viewing by a user, the load record may present a representation of the thumbnail image with the other contents of the load record. In this manner, the user may view the parameters associated with a load, as entered by a user, as well as the actual monitor run through the sterilizer with the load.

The thumbnail image may include a hypertext link that permits the user to click on the thumbnail image to thereby view the full resolution scanned digital image. In some embodiments, the thumbnail image may have sufficient resolution and size to permit accurate assessment of the monitor from which the scanned image was made. In many cases, however, inspection of the full resolution image may be desirable to ensure an accurate evaluation of the state of the pertinent sterilizer. Both the thumbnail and the full resolution image may be color images, or monochromatic images if sufficient to view the necessary indications presented by the monitor.

Figure 24:
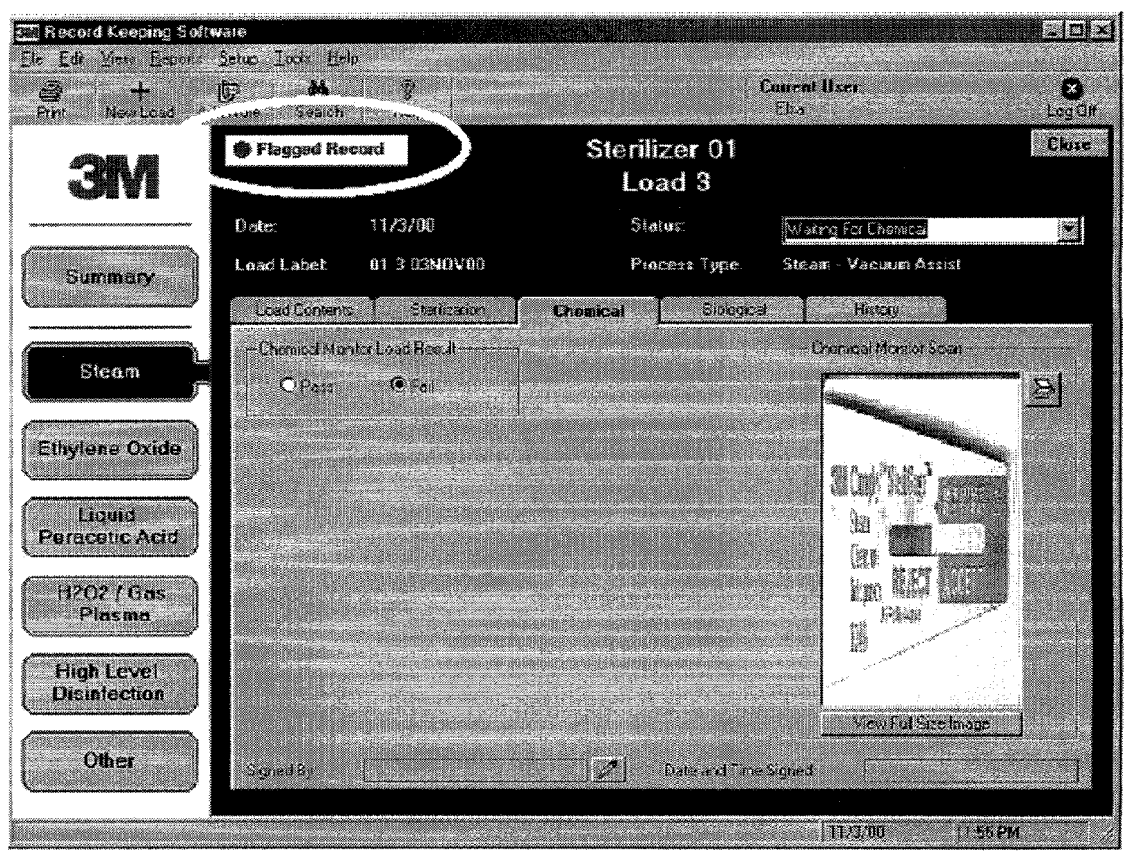
FIG. 24 illustrates an example user interface screen presenting an electronic sterilization record with a scanned chemical monitor.

FIG. 24 illustrates an example user interface screen presenting an electronic sterilized load record with a chemical monitor window. As shown in FIG. 24, when a user clicks on the "chemical" tab of the load record, system 10 presents an indication of whether the load passed or failed the chemical monitor test, as entered by a technician. The load record may be flagged for any failed result. System 10 also presents a thumbnail image of the actual chemical monitor that was evaluated by the technician. Again, the load record may provide an embedded hypertext link within the thumbnail image or a button ("View Full Size Image") that can be selected by the user to access the full resolution and full size version of the chemical monitor image.

Figure 25:
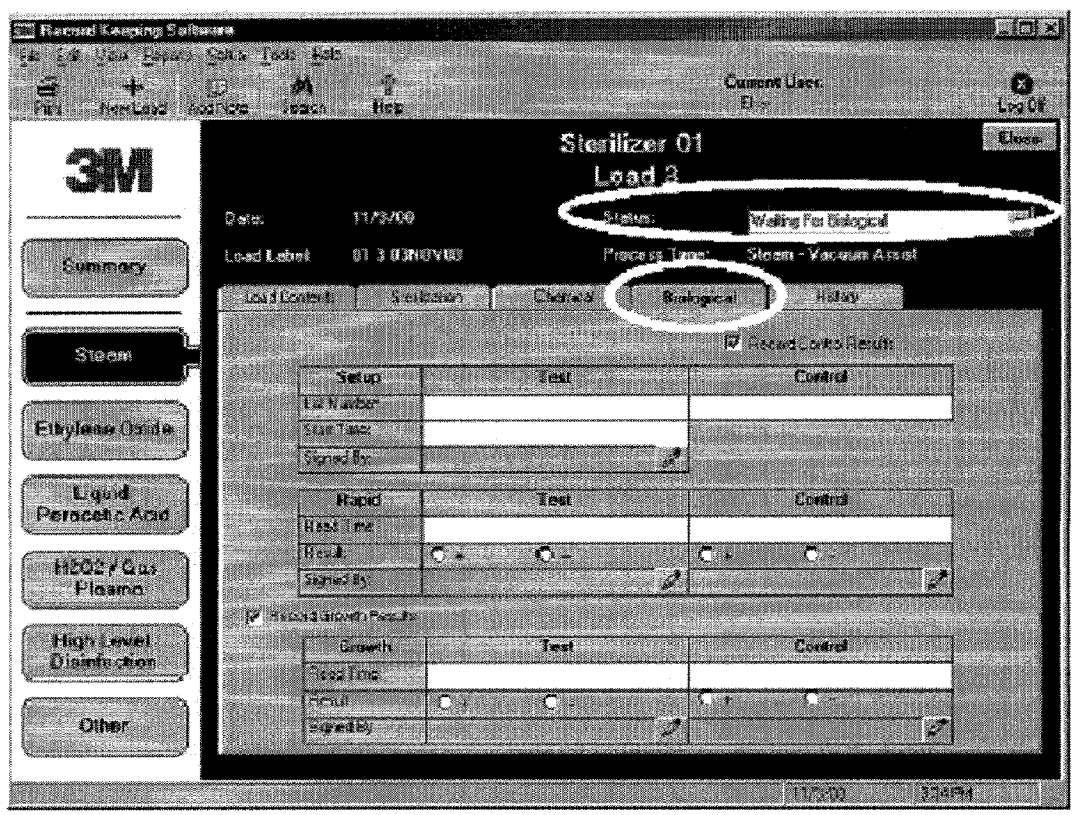
FIG. 25 illustrates an example user interface screen presenting an electronic sterilization record with a biological monitor recording area.

FIG. 25 illustrates an example user interface screen presenting an electronic sterilized load record with biological monitor window. As shown in FIG. 25, when a user clicks on the "Biological" tab of the load record, system 10 presents window for entry of information taken from a biological monitor run. For example, the user may enter a test lot number in the "Lot Number" field, and the start time of the test in the "Start Time" field. In addition, the user may click on the "pencil" icon to sign off on the entries. As further shown in FIG. 25, when "Rapid" results are complete, the user may enter the read times for the test and control monitors. With respect to growth results, the user enters the read time for the test and control monitors, along with a positive or negative sign to indicate whether growth was indicated by the monitors. Again, the user can click the pencil icons in the "Setup," "Rapid," and "Growth" areas to sign off on the biological monitor results.

Figure 26:
FIG. 26 illustrates an example user interface screen presenting an electronic sterilization record with a scanned Bowie-Dick type test indicator.

FIG. 26 illustrates an example user interface screen presenting an electronic sterilized load record with a Bowie-Dick type window. As shown in FIG. 26, when a user clicks on the "Bowie-Dick Type" tab of the load record, system 10 presents an indication of whether the load passed or failed the Bowie-Dick type test, as entered by a technician. If the Bowie-Dick type test is selected for the load, chemical and biological monitors typically will not be used. Hence, there is no chemical or biological tab in FIG. 26. Also, system 10 presents a thumbnail, i.e., reduced resolution, image of the actual Bowie-Dick test result that was evaluated by the technician. The load record may provide an embedded hypertext link within the thumbnail image or, as shown in FIG. 26, a button ("View Full Size Image") that can be selected by the user to access the full resolution and full size version of the Bowie-Dick type test results.

Associating a scanned image of a sterilization indicator such as a sterilizer strip, chemical monitor, Bowie-Dick type test result, or the like with an electronic sterilized load record, as described herein, provides a persistent record of the actual sterilization monitor evaluated by a user to render a pass/fail decision. The image is conveniently accessible by other users, including supervisors, quality control personnel, and audit personnel.

Unlike the original sterilization monitor, the scanned sterilization monitor image is not prone to degradation such as fading, curling, reverse color change, or other damage that can affect accuracy. Instead, the scanned image provides a static copy that indicates the actual condition of the sterilization monitor at the time of use. Also, the scanned sterilization monitor image cannot be misplaced, and is less likely to be filed incorrectly. Rather, the scanned image can be maintained electronically on a long-term basis within sterilization information archive 22.

Thus, for quality review or audit purposes, another user may retrieve a sterilization record from the archive 22 and compare the information entered earlier by a different user to the condition indicated by the scanned sterilization monitor. Advantageously, the comparison may even be performed remotely, e.g., over a network connection, even by audit personnel who are not members of the sterilization facility or department staff. The ability of an original user to annotate the electronic sterilization record or the scanned monitor itself may further aid subsequent reviewers in their analysis.

Figure 27:
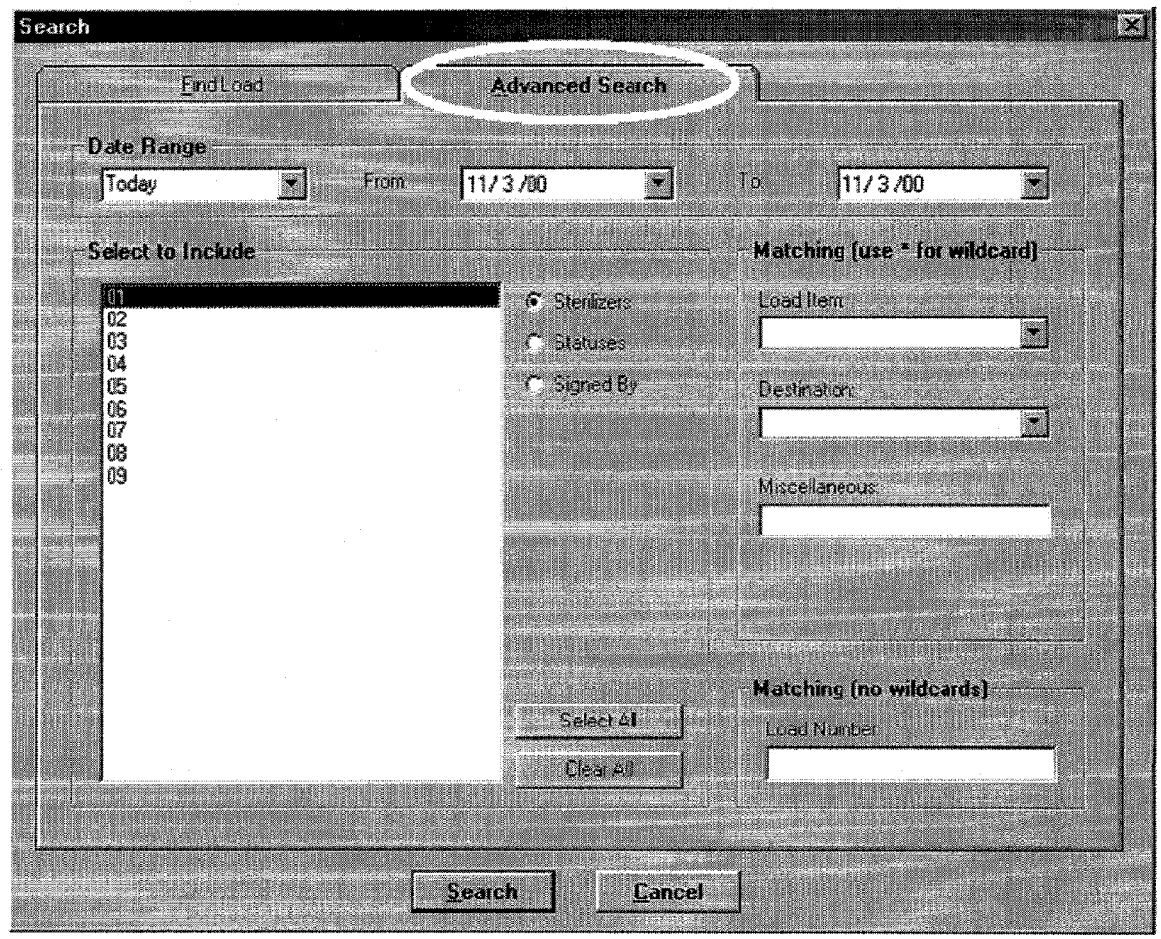
FIG. 27 illustrates an example user interface screen presenting a search engine feature.

FIG. 27 illustrates an example user interface screen presenting a search engine feature. Using the search engine, a user may locate sterilized load records according to variety of criteria including date of processing, sterilizer used in processing, type of load item, destination, load number, and even key word inclusion. The criteria can be combined or selected individually for a search, enabling retrieval of a vast array of load records for different purposes such as-comparative analysis, quality control, regulatory reporting and the like. The search may be executed by processor 12 (FIG. 1) based on search criteria entered by a user. Using the search criteria, processor 12 may search a database that tracks the file locations of sterilized load records within sterilization information archive 22 (FIG. 1) according to data in database fields that match the search criteria.

Figure 28:
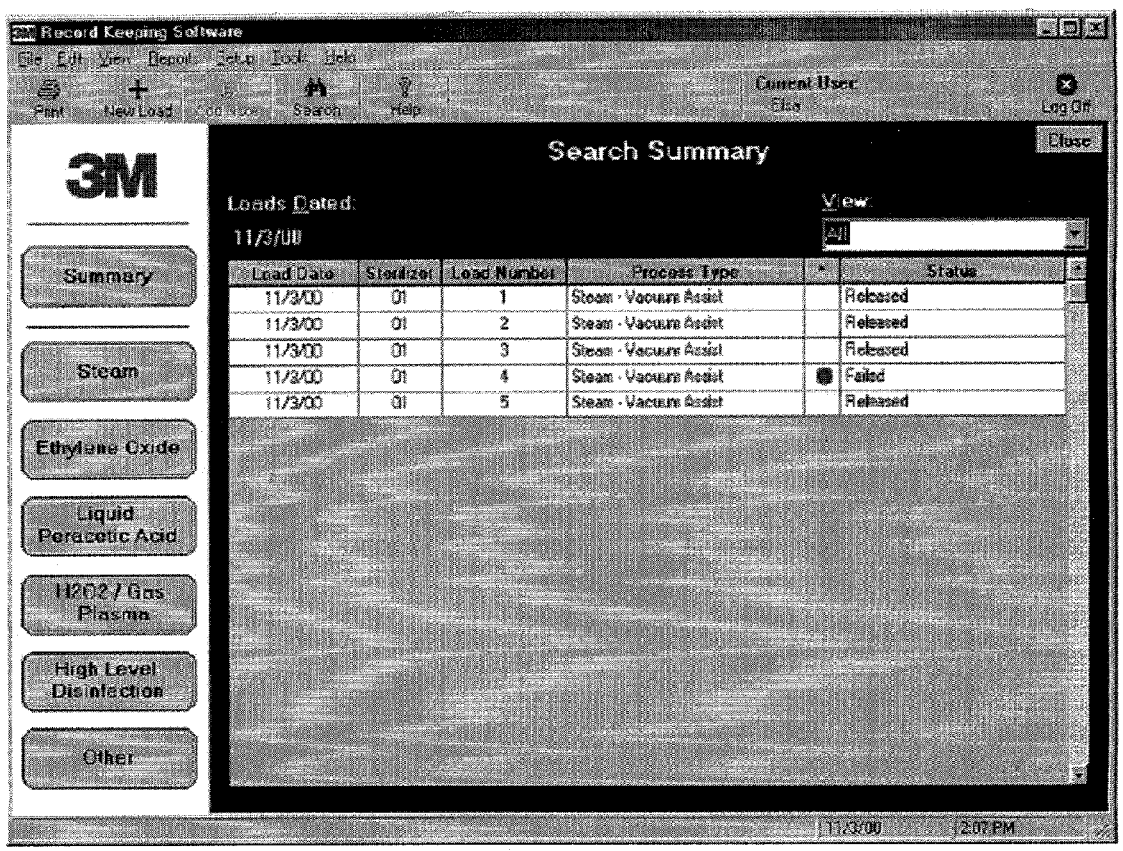
FIG. 28 illustrates an example user interface screen presenting search results.

FIG. 28 illustrates an example user interface screen presenting search results. In particular, FIG. 28 depicts a search summary screen that shows all loads processed on a given date, "Nov. 3, 2000" in the example of FIG. 28. The search summary screen may provide information about the loads, including load number, process type, and load status, e.g., in process, released, failed. Other information may be presented at the election of the user.

FIGS. 29-35 illustrate portions of user interface screens presenting reports for a variety of search criteria. Ordinarily, the user may desire that the search results be limited to a particular date range. The report capability of system 10 may aid sterilization department management in monitoring quality, workload, and throughput issues, in order to effectively manage facility resources and take corrective action to improve quality.

In the example of FIG. 29, the user interface screen provides a report of final load status designations by each of several operators, i.e., users. The example report in the user interface screen of FIG. 29 lists the operators by name, and indicates how many loads were passed, released, aborted, quarantined, failed or recalled. In addition, the report may detail the type of tests passed, e.g., Bowie-Dick type. This type of report may aid in detecting process quality control issues among individual users, and could suggest the need for tighter controls, enhanced supervision, or added training.

In the example of FIG. 30, the user interface screen provides a report of processing history by biological test and control results for different sterilizers. In this example, the report lists sterilizers by ID code, type of process, and number of BI (biological monitor) loads, and provides rapid results and growth results. The example of FIG. 31 is similar to that of FIG. 30, but shows processing history for sterilizers according to Bowie-Dick type test results.

FIG. 32 depicts an exemplary report conveying processing history according to destination. In particular, the report lists a number destinations by name, and indicates the total number of load items processed for the destination, and the process types used. In addition, the report could identify the sterilizers from which load items were delivered.

FIG. 33 depicts an exemplary report conveying processing history according to load item. This report may list a number of load items by type or name, and indicate the number of times the load item was processed during a given period of time. This type of report may aid in identifying traffic and throughput trends within the sterilization facility.

FIG. 34 depicts an exemplary report conveying processing history according to sterilizer. This report may list a number of sterilizers by ID code and process type, and indicate the number of loads processed, released, aborted, quarantined, failed, and recalled as well as whether particular types of tests, e.g., Bowie-Dick type, were passed.

FIG. 35 depicts an exemplary report conveying processing history according to process parameters. This report may list a number sterilizers by ID code and process type, and high- light passed loads versus failed loads for the sterilizers. This type of report may aid in identification of process quality control issues for a particular sterilizer.

Various embodiments of the invention have been described. These and other embodiments are within the scope of the following claims.

The invention claimed is:

1. A method comprising:
    generating an electronic sterilization record for a sterilized load;
    optically scanning a sterilization monitor associated with the sterilized load;
    storing a digital representation of the scanned sterilization monitor; and
    associating the stored digital representation with the electronic sterilization record,
    wherein the sterilization monitor visibly indicates a result representing a sterilization condition of the sterilized load.

2. The method of claim 1, wherein the sterilization monitor includes one of a chemical monitor, a Bowie-Dick type monitor, and a sterilizer strip.

3. The method of claim 1, further comprising:
    receiving information from a user indicating a sterilization condition of the sterilized load; and
    associating the received information with the electronic sterilization record.

4. The method of claim 3, further comprising verifying an authorization status of the user before associating the received information with the electronic sterilization record.

5. The method of claim 1, further comprising:
    receiving information from a first user indicating a sterilization condition of the sterilized load;
    associating the information with the electronic sterilization record; and
    displaying contents of the electronic sterilization record and the digital representation of the scanned sterilization monitor for review by a second user.

6. The method of claim 1, further comprising displaying contents of the electronic sterilization record and the digital representation of the scanned sterilization monitor for viewing by a user.

7. The method of claim 1, wherein the electronic sterilization record includes process information including at least one of process type, sterilizer identification, and cycle parameters.

8. The method of claim 1, further comprising:
    generating electronic sterilization records for multiple sterilized loads;
    optically scanning sterilization monitors associated with each of the sterilized loads;
    storing digital representations of the scanned sterilization monitor; and
    associating the stored digital representations with the electronic sterilization records corresponding to the pertinent sterilized loads.

9. The method of claim 8, further comprising generating a report containing selected information from the electronic sterilization records.

10. The method of claim 1, wherein the electronic sterilization record contains high level disinfection information for the sterilized load.

11. A system comprising:
    a computer that generates an electronic sterilization record for a sterilized load;
    a scanner that optically scans a sterilization monitor associated with the sterilized load; and a storage device that stores a digital representation of the scanned sterilization monitor, wherein the computer associates the digital representation with the electronic sterilization record, and wherein the sterilization monitor visibly indicates a result representing a sterilization condition of the sterilized load.

12. The system of claim 11, wherein the sterilization monitor includes one of a chemical monitor, a Bowie-Dick type monitor, and a sterilizer strip.

13. The system of claim 11, further comprising an input device that receives information from a user indicating a sterilization condition of the sterilized load, wherein the computer associates the received information with the electronic sterilization record.

14. The system of claim 13, wherein the computer verifies an authorization status of the user before associating the received information with the electronic sterilization record.

15. The system of claim 11, further comprising:
an input device that receives information from a first user indicating a sterilization condition of the sterilized load, wherein the computer associates the information with the electronic sterilization record; and
a display device that displays contents of the electronic sterilization record and the digital representation of the scanned sterilization monitor for review by a second user.

16. The system of claim 11, further comprising a display device that displays contents of the electronic sterilization record and the digital representation of the scanned sterilization monitor for viewing by a user.

17. The system of claim 11, wherein the electronic sterilization record includes process information including at least one of process type, sterilizer identification, and cycle parameters.

18. The system of claim 11, wherein the computer generates electronic sterilization records for multiple sterilized loads, the scanner optically scans sterilization monitors associated with each of the sterilized loads, and the storage device stores digital representations of the scanned sterilization monitor, the computer associating the stored digital representations with the electronic sterilization records corresponding to the pertinent sterilized loads.

19. The system, of claim 18, wherein the computer generates a report containing selected information from the electronic sterilization records.

20. The system of claim 11, wherein the electronic sterilization record contains high level disinfection information for the sterilized load.

21. A computer-readable medium carrying instructions to cause a programmable processor to:
generate an electronic sterilization record for a sterilized load;
control a scanner to optically scan a sterilization monitor associated with the sterilized load;
store a digital representation of the scanned sterilization monitor; and
associate the digital representation with the electronic sterilization record,
wherein the sterilization monitor visibly indicates a result representing a sterilization condition of the sterilized load.

22. The computer-readable medium of claim 21, wherein the sterilization monitor includes one of a chemical monitor, a Bowie-Dick type monitor, and a sterilizer strip.

23. The computer-readable medium of claim 21, wherein the instructions cause a programmable processor to:
receive information from a user indicating a sterilization condition of the sterilized load; and
associate the received information with the electronic sterilization record.

24. The computer-readable medium of claim 23, wherein the instructions cause a programmable processor to verify an authorization status of the user before associating the received information with the electronic sterilization record.

25. The computer-readable medium of claim 21, wherein the instructions cause a programmable processor to:
receive information from a first user indicating a sterilization condition of the sterilized load;
associate the information with the electronic sterilization record; and
display contents of the electronic sterilization record and the digital representation of the scanned sterilization monitor for review by a second user.

26. The computer-readable medium of claim 21, wherein the instructions cause a programmable processor to display contents of the electronic sterilization record and the digital representation of the scanned sterilization monitor for viewing by a user.

27. The computer-readable medium of claim 21, wherein the electronic sterilization record includes process information including at least one of process type, sterilizer identification, and cycle parameters.

28. The computer-readable medium of claim 21, wherein the instructions cause a programmable processor to:
generate electronic sterilization records for multiple sterilized loads;
control the scanner to optically scan sterilization monitors associated with each of the sterilized loads;
store digital representations of the scanned sterilization monitor; and
associate the digital representations with the electronic sterilization records corresponding to the pertinent sterilized loads.

29. The computer-readable medium of claim 28, wherein the instructions cause a programmable processor to generate a report containing selected information from the electronic sterilization records.

30. The computer-readable medium of claim 21, wherein the electronic sterilization record contains high level disinfection information for the sterilized load.

31. A method comprising:
generating an electronic sterilization record for a sterilized load;
optically scanning a sterilization monitor associated with the sterilized load;
storing a digital representation of the scanned sterilization monitor;
associating the stored digital representation with the electronic sterilization record;
receiving information from a first user indicating a sterilization condition of the sterilized load;
associating the received information with the electronic sterilization record; and
presenting the electronic sterilization record to a second user for comparison of the information received from the first user to the digital representation of the scanned sterilization monitor.

32. The method of claim 31, wherein the sterilization monitor includes one of a chemical monitor, a Bowie-Dick type monitor, and a sterilizer strip.

33. A system comprising:
a computer that generates an electronic sterilization record for a sterilized load;

an optical scanner that scans a sterilization monitor associated with the sterilized load, wherein the computer stores a digital representation of the scanned sterilization monitor, and associates the digital representation with the electronic sterilization record;

a user input device that receives information from a first user indicating a sterilization condition of the sterilized load, wherein the computer associates the received information with the electronic sterilization record; and a user output device that presents the electronic sterilization record to a second user for comparison of the information received from the first user to the stored digital representation of the scanned sterilization monitor.

34. The system of claim 33, wherein the sterilization monitor includes one of a chemical monitor, a Bowie-Dick type monitor, and a sterilizer strip.

35. A computer-readable medium carrying instructions to cause a programmable processor to:

generate an electronic sterilization record for a sterilized load;

control an optical scanner to scan a sterilization monitor associated with the sterilized load;

store a digital representation of the scanned sterilization monitor;

associate the stored digital representation with the electronic sterilization record;

receive information from a first user indicating a sterilization condition of the sterilized load;

associate the received information with the electronic sterilization record; and present the electronic sterilization record to a second user for comparison of the information received from the first user to the stored digital representation of the scanned sterilization monitor.

36. The medium of claim 35, wherein the sterilization monitor includes one of a chemical monitor, a Bowie-Dick type monitor, and a sterilizer strip.

37. A method comprising:

generating an electronic sterilization record for a sterilized load;

optically scanning a sterilization monitor associated with the sterilized load;

storing a digital representation of the scanned sterilization monitor;

associating the stored digital representation with the electronic sterilization record;

receiving information from a first user indicating a sterilization condition of the sterilized load;

associating the information with the electronic sterilization record; and displaying contents of the electronic sterilization record and the digital representation of the scanned sterilization monitor for review by a second user.

38. A system comprising:

a computer that generates an electronic sterilization record for a sterilized load;

a scanner that optically scans a sterilization monitor associated with the sterilized load;

a storage device that stores a digital representation of the scanned sterilization monitor, wherein the computer associates the digital representation with the electronic sterilization record;

an input device that receives information from a first user indicating a sterilization condition of the sterilized load, wherein the computer associates the information with the electronic sterilization record; and a display device that displays contents of the electronic sterilization record and the digital representation of the scanned sterilization monitor for review by a second user.

39. A computer-readable medium carrying instructions to cause a programmable processor to:

generate an electronic sterilization record for a sterilized load;

control a scanner to optically scan a sterilization monitor associated with the sterilized load;

store a digital representation of the scanned sterilization monitor;

associate the digital representation with the electronic sterilization record;

receive information from a first user indicating a sterilization condition of the sterilized load;

associate the information with the electronic sterilization record; and display contents of the electronic sterilization record and the digital representation of the scanned sterilization monitor for review by a second user.

* * * * *

UNITED STATES PATENT AND TRADEMARK OFFICE
CERTIFICATE OF CORRECTION

| | | |
|---|---|---|
| PATENT NO. | : 7,899,681 B2 | Page 1 of 1 |
| APPLICATION NO. | : 10/113923 | |
| DATED | : March 1, 2011 | |
| INVENTOR(S) | : Kevin R Katzenmaier | |

It is certified that error appears in the above-identified patent and that said Letters Patent is hereby corrected as shown below:

Column 17
Line 5, Delete "as-comparative" and insert in place thereof -- as comparative --.

Column 19
Claim 19, Line 44, Delete "system," and insert in place thereof -- system --.

Signed and Sealed this
Twenty-fourth Day of April, 2012

David J. Kappos
*Director of the United States Patent and Trademark Office*